(12) United States Patent
Goldstein et al.

(10) Patent No.: US 8,138,315 B2
(45) Date of Patent: Mar. 20, 2012

(54) ANTI-ALPHA V IMMUNOLIPOSOME COMPOSITIONS, METHODS AND USES

(75) Inventors: Joshua Goldstein, Radnor, PA (US); Allen Magill, Radnor, PA (US); Deepak Saini, Radnor, PA (US); Linda A. Snyder, Radnor, PA (US); Raymond Sweet, Radnor, PA (US); Steve P. Weng, Fremont, CA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 0 days.

(21) Appl. No.: 13/105,643

(22) Filed: May 11, 2011

(65) Prior Publication Data

US 2011/0268655 A1 Nov. 3, 2011

Related U.S. Application Data

(62) Division of application No. 12/118,994, filed on May 12, 2008, now abandoned.

(60) Provisional application No. 60/917,397, filed on May 11, 2007.

(51) Int. Cl.
*C12P 21/08* (2006.01)

(52) U.S. Cl. ............... 530/387.3; 530/391.1; 530/391.3; 530/391.7

(58) Field of Classification Search ........... 530/387.3, 530/391.1, 391.3, 391.7
See application file for complete search history.

(56) References Cited

U.S. PATENT DOCUMENTS

| | | | |
|---|---|---|---|
| 5,013,556 | A | 5/1991 | Woodle et al. |
| 5,260,203 | A | 11/1993 | Ladner et al. |
| 5,985,278 | A | 11/1999 | Mitjans et al. |
| 7,163,681 | B2 | 1/2007 | Giles-Komar et al. |
| 2003/0040044 | A1 | 2/2003 | Heavner et al. |
| 2004/0185507 | A1* | 9/2004 | Giles-Komar et al. ........ 435/7.2 |
| 2006/0127407 | A1 | 6/2006 | Chen et al. |
| 2006/0206947 | A1 | 9/2006 | Scallon et al. |
| 2007/0010016 | A1 | 1/2007 | McCelland et al. |

FOREIGN PATENT DOCUMENTS

| | | |
|---|---|---|
| WO | WO 99/55367 A1 | 11/1999 |
| WO | WO 99/56129 A1 | 11/1999 |
| WO | WO 02/12501 A2 | 2/2002 |
| WO | WO 2004/076658 A1 | 9/2004 |
| WO | WO 2006/104677 A2 | 10/2006 |

OTHER PUBLICATIONS

Klibanov et al., Biochim Biophys. Acta. 1062: pp. 142-148 (1991).
Hansen et al., Biochim. Biophys. Acta. 1239: pp. 133-144 (1995).
Allen et al., Biochim. Biophys Acta.1237: pp. 9-109 (1995).
Blume et al., Biochim Biophys. Acta. 1149: pp. 180-184 (1993).
Bejeck et al., Cancer Research, vol. 55, pp. 2346-2351 (Jun. 1995).
Padiolleua-Lefever et al., Molecular Immunology, pp. 1888-1896 (2006).

* cited by examiner

*Primary Examiner* — Misook Yu
*Assistant Examiner* — Brad Duffy
(74) *Attorney, Agent, or Firm* — Kenneth J. Dow

(57) ABSTRACT

An immunoliposome composition targeted to the alphaV-integrin subunit of integrin receptors comprised of ligand-targeted liposomes bearing at least one targeting-ligand derived from an antibody and having binding specificity for at least one integrin receptor comprising an alpha V subunit including $\alpha v \beta 1$, $\alpha v \beta 3$ $\alpha v \beta 5$, $\alpha v \beta 6$, or $\alpha v \beta 8$ integrin cell receptors is described. The antibody-derived targeting ligand may be a Fab' fragment, a scFv, or the like. Binding of the immunoliposome to $\alpha v$-integrin expressing cells, preferably results in internalization of the immunoliposome for cytoplasmic delivery of a liposome-entrapped agent.

8 Claims, 22 Drawing Sheets

Fig. 2A 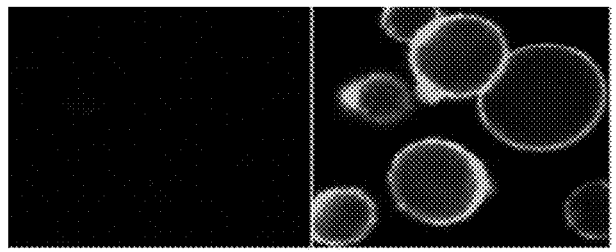 Fig. 2C
Fig. 2B 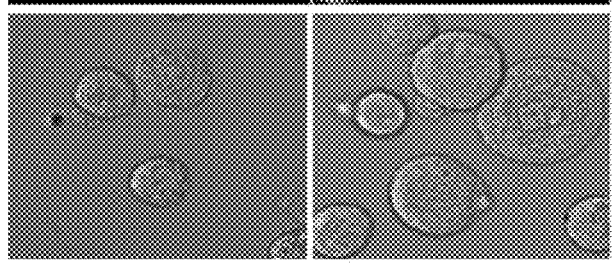 Fig. 2D

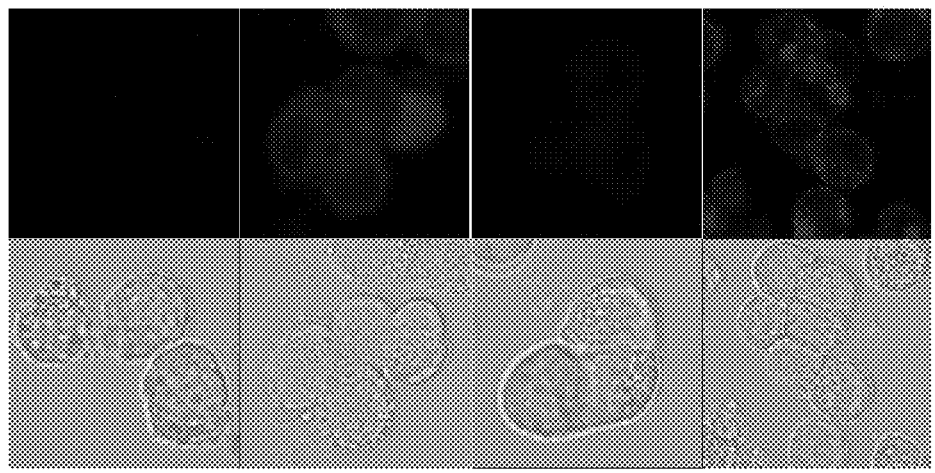

Fig. 4A    Fig. 4C    Fig. 4E    Fig. 4G    Fig. 4I
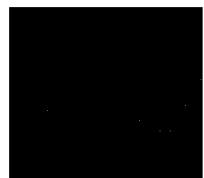 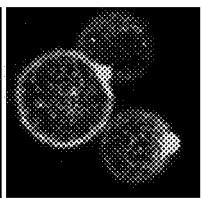 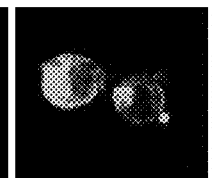 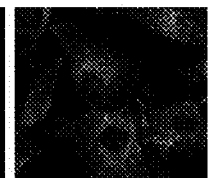 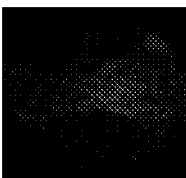
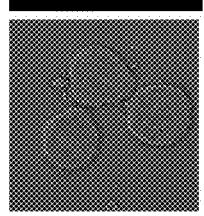 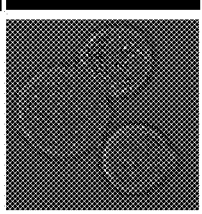 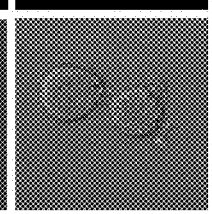 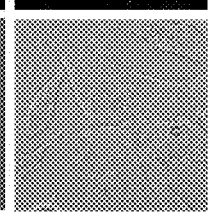 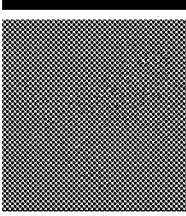
Fig. 4B    Fig. 4D    Fig. 4F    Fig. 4H    Fig. 4J Fig. 5A  Fig. 5C  Fig. 5E  Fig. 5G
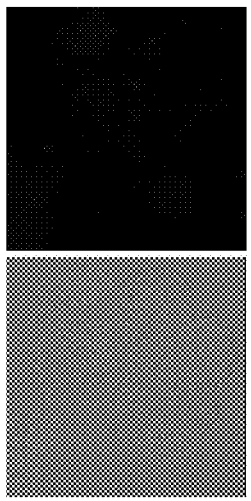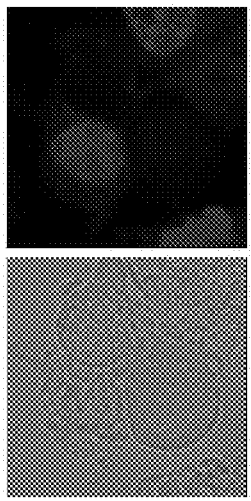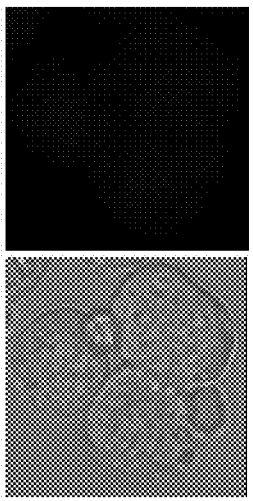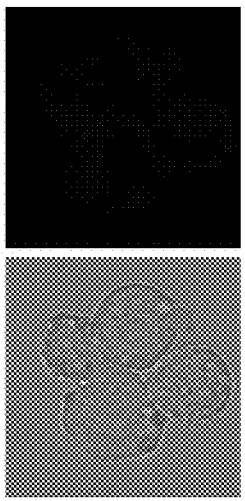
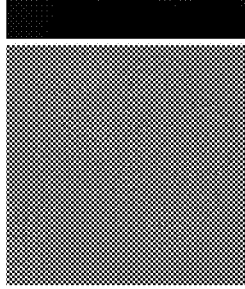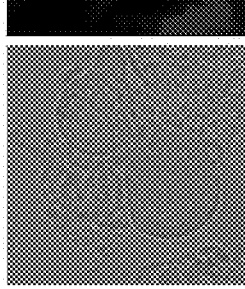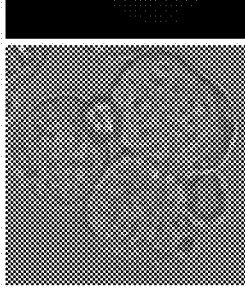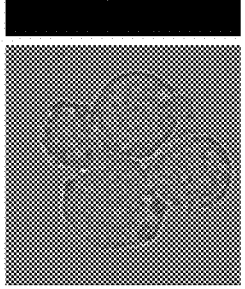
Fig. 5B  Fig. 5D  Fig. 5F  Fig. 5H alphaVbeta5

SEQUENCE LISTING

```
<160> NUMBER OF SEQ ID NOS: 11

<210> SEQ ID NO 1
<211> LENGTH: 449
<212> TYPE: PRT
<213> ORGANISM: Homo sapiens

<400> SEQUENCE: 1
```

```
Gln Val Gln Leu Val Glu Ser Gly Gly Val Val Gln Pro Gly Arg
  1               5                  10                 15

Ser Arg Arg Leu Ser Cys Ala Ala Ser Gly Phe Thr Phe Ser Arg Tyr
             20                  25                  30

Thr Met His Trp Val Arg Gln Ala Pro Gly Lys Gly Leu Glu Trp Val
         35                  40                  45

Ala Val Ile Ser Phe Asp Gly Ser Asn Lys Tyr Tyr Val Asp Ser Val
     50                  55                  60

Lys Gly Arg Phe Thr Ile Ser Arg Asp Asn Ser Glu Asn Thr Leu Tyr
 65                  70                  75                  80

Leu Gln Val Asn Ile Leu Arg Ala Glu Asp Thr Ala Val Tyr Tyr Cys
                 85                  90                  95

Ala Arg Glu Ala Arg Gly Ser Tyr Ala Phe Asp Ile Trp Gly Gln Gly
             100                 105                 110

Thr Met Val Thr Val Ser Ser Ala Ser Thr Lys Gly Pro Ser Val Phe
             115                 120                 125

Pro Leu Ala Pro Ser Ser Lys Ser Thr Ser Gly Gly Thr Ala Ala Leu
         130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Asp Lys
 210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
             245                 250                 255

Arg Thr Pro Glu Val Thr Cys Val Val Val Asp Val Ser His Glu Asp
         260                 265                 270

Pro Glu Val Lys Phe Asn Trp Tyr Val Asp Gly Val Glu Val His Asn
     275                 280                 285

Ala Lys Thr Lys Pro Arg Glu Glu Gln Tyr Asn Ser Thr Tyr Arg Val
 290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
             325                 330                 335

Thr Ile Ser Lys Ala Lys Gly Gln Pro Arg Glu Pro Gln Val Tyr Thr
         340                 345                 350

Leu Pro Pro Ser Arg Asp Glu Leu Thr Lys Asn Gln Val Ser Leu Thr
     355                 360                 365

Cys Leu Val Lys Gly Phe Tyr Pro Ser Asp Ile Ala Val Glu Trp Glu
 370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
             405                 410                 415

Ser Arg Trp Gln Gln Gly Asn Val Phe Ser Cys Ser Val Met His Glu
         420                 425                 430
```

Ala Leu His Asn His Tyr Thr Gln Lys Ser Leu Ser Leu Ser Pro Gly
            435                 440                 445
Lys

<210> SEQ ID NO 2
<211> LENGTH: 215
<212> TYPE: PRT
<213> ORGANISM: Homo sapiens

<400> SEQUENCE: 2

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 3
<211> LENGTH: 231
<212> TYPE: PRT
<213> ORGANISM: Homo sapiens

<400> SEQUENCE: 3

Gln Val Gln Leu Val Glu Ser Gly Gly Gly Val Val Gln Pro Gly Arg
  1               5                  10                  15

Ser Arg Arg Leu Ser Cys Ala Ala Ser Gly Phe Thr Phe Ser Arg Tyr
             20                  25                  30

Thr Met His Trp Val Arg Gln Ala Pro Gly Lys Gly Leu Glu Trp Val
         35                  40                  45

Ala Val Ile Ser Phe Asp Gly Ser Asn Lys Tyr Tyr Val Asp Ser Val
     50                  55                  60

Lys Gly Arg Phe Thr Ile Ser Arg Asp Asn Ser Glu Asn Thr Leu Tyr
 65                  70                  75                  80

Leu Gln Val Asn Ile Leu Arg Ala Glu Asp Thr Ala Val Tyr Tyr Cys

```
                     85                  90                  95
Ala Arg Glu Ala Arg Gly Ser Tyr Ala Phe Asp Ile Trp Gly Gln Gly
                    100                 105                 110

Thr Met Val Thr Val Ser Ser Ala Ser Thr Lys Gly Pro Ser Val Phe
                    115                 120                 125

Pro Leu Ala Pro Ser Ser Lys Ser Thr Ser Gly Gly Thr Ala Ala Leu
                    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                    180                 185                 190

Ser Ser Leu Gly Thr Gln Thr Tyr Ile Cys Asn Val Asn His Lys Pro
                    195                 200                 205

Ser Asn Thr Lys Val Asp Lys Lys Val Glu Pro Lys Ser Cys Asp Lys
                    210                 215                 220

Thr His Thr Cys Pro Gly Lys
225                 230

<210> SEQ ID NO 4
<211> LENGTH: 275
<212> TYPE: PRT
<213> ORGANISM: Artificial Sequence
<220> FEATURE:
<223> OTHER INFORMATION: Construct comprising human immunogobulin
      regions and artifical sequences
<220> FEATURE:
<221> NAME/KEY: SIGNAL
<222> LOCATION: (1)..(22)
<223> OTHER INFORMATION: pelB
<220> FEATURE:
<221> NAME/KEY: BINDING
<222> LOCATION: (23)..(141)
<223> OTHER INFORMATION: CNTO95 heavy chain variable region
<220> FEATURE:
<221> NAME/KEY: BINDING
<222> LOCATION: (143)..(156)
<223> OTHER INFORMATION: flexible linker sequence of 3 X GGGS
<220> FEATURE:
<221> NAME/KEY: BINDING
<222> LOCATION: (157)..(264)
<223> OTHER INFORMATION: CNTO95 light chain variable region
<220> FEATURE:
<221> NAME/KEY: BINDING
<222> LOCATION: (265)..(270)
<223> OTHER INFORMATION: Purification sequence
<220> FEATURE:
<221> NAME/KEY: BINDING
<222> LOCATION: (271)..(275)
<223> OTHER INFORMATION: Conjugation region

<400> SEQUENCE: 4

Met Lys Tyr Leu Leu Pro Thr Ala Ala Ala Gly Leu Leu Leu Leu Ala
1                   5                   10                  15

Ala Gln Pro Ala Met Ala Gln Val Gln Leu Val Glu Ser Gly Gly Gly
                    20                  25                  30

Val Val Gln Pro Gly Arg Ser Leu Arg Leu Ser Cys Ala Ala Ser Gly
                    35                  40                  45

Phe Thr Phe Ser Arg Tyr Thr Met His Trp Val Arg Gln Ala Pro Gly
                    50                  55                  60

Lys Gly Leu Glu Trp Val Ala Val Ile Ser Phe Asp Gly Ser Asn Lys
65                  70                  75                  80

Tyr Tyr Val Asp Ser Val Lys Gly Arg Phe Thr Ile Ser Arg Asp Asn
```

```
                        85                  90                  95
Ser Glu Asn Thr Leu Tyr Leu Gln Val Asn Ile Leu Arg Ala Glu Asp
            100                 105                 110

Thr Ala Val Tyr Tyr Cys Ala Arg Glu Ala Arg Gly Ser Tyr Ala Phe
            115                 120                 125

Asp Ile Trp Gly Gln Gly Thr Met Val Thr Val Ser Ser Gly Gly Gly
            130                 135                 140

Gly Ser Gly Gly Gly Gly Ser Gly Gly Gly Ser Glu Ile Val Leu
145                 150                 155                 160

Thr Gln Ser Pro Ala Thr Leu Ser Leu Ser Pro Gly Glu Arg Ala Thr
                165                 170                 175

Leu Ser Cys Arg Ala Ser Gln Ser Val Ser Ser Tyr Leu Ala Trp Tyr
                180                 185                 190

Gln Gln Lys Pro Gly Gln Ala Pro Arg Leu Leu Ile Tyr Asp Ala Ser
                195                 200                 205

Asn Arg Ala Thr Gly Ile Pro Ala Arg Phe Ser Gly Ser Gly Ser Gly
                210                 215                 220

Thr Asp Phe Thr Leu Thr Ile Ser Ser Leu Glu Pro Glu Asp Phe Ala
225                 230                 235                 240

Val Tyr Tyr Cys Gln Gln Arg Ser Asn Trp Pro Pro Phe Thr Phe Gly
                245                 250                 255

Pro Gly Thr Lys Val Asp Ile Lys His His His His His Gly Gly
                260                 265                 270

Gly Gly Cys
        275

<210> SEQ ID NO 5
<211> LENGTH: 893
<212> TYPE: DNA
<213> ORGANISM: Artificial Sequence
<220> FEATURE:
<223> OTHER INFORMATION: human codons replaced with E. coli preferred
      codons
<220> FEATURE:
<221> NAME/KEY: sig_peptide
<222> LOCATION: (57)..(122)
<223> OTHER INFORMATION: pelB signal
<220> FEATURE:
<221> NAME/KEY: terminator
<222> LOCATION: (882)..(887)
<223> OTHER INFORMATION: Tandem stop codons

<400> SEQUENCE: 5
gaattctatg gaacgataaa tgcccatgaa aattctattt caaggagaca gtcataatga      60
aataccTgct gccgaccgct gctgctggtc tgctgctgct ggcggcccag ccggccatgg     120
ctcaggtgca gctggtggag tctggtggtg gcgtggtcca gctggtcgt tcccgtcgcc     180 tctcctgtgc agcctctggt ttcaccttca gtcgttatac tatgcactgg gtccgccagg     240
ctccaggcaa gggtctggag tgggtggcag ttatctcatt tgatggtagc aacaaatact     300
acgtagactc cgtgaagggc cgtttcacca tctcccgtga caactccgag aacacgctgt     360
atctgcaagt gaacatcctg cgtgctgagg acacggctgt gtattactgt gcgcgtgagg     420
cccgtggttc ctatgctttt gatatctggg gccaaggtac catggtcacc gtctcttccg     480
gtggcggtgg ctccggtggc ggtggctccg gtggcggtga tccgaaatt gtgctgaccc     540 agtctccagc cacccTgtct ctgtctccag gtgaacgtgc caccctctcc tgccgtgcca     600
gtcagagtgt tagcagctac ctggcctggt accaacagaa acctggccag gctccgcgtc     660
tcctcatcta tgatgcatcc aaccgtgcca ctggcatccc agcccgtttc agtggcagtg     720
```

```
gttctggtac cgacttcact ctcaccatca gcagcctgga gcctgaagat tttgcagttt    780
attactgtca gcagcgtagc aactggcctc cattcacttt cggccctggt accaaagtgg    840
atatcaaaca ccaccatcac caccatggtg gtggtggttg ctaataactc gag            893
```

```
<210> SEQ ID NO 6
<211> LENGTH: 5
<212> TYPE: PRT
<213> ORGANISM: Homo sapiens

<400> SEQUENCE: 6

Gly Gly Gly Gly Ser
1               5

<210> SEQ ID NO 7
<211> LENGTH: 5
<212> TYPE: PRT
<213> ORGANISM: Homo sapiens

<400> SEQUENCE: 7

Gly Gly Gly Gly Ser
1               5

<210> SEQ ID NO 8
<211> LENGTH: 5
<212> TYPE: PRT
<213> ORGANISM: Homo sapiens

<400> SEQUENCE: 8

Gly Gly Gly Gly Ser
1               5

<210> SEQ ID NO 9
<211> LENGTH: 5
<212> TYPE: PRT
<213> ORGANISM: Homo sapiens

<400> SEQUENCE: 9

Gly Gly Gly Gly Ser
1               5

<210> SEQ ID NO 10
<211> LENGTH: 98
<212> TYPE: PRT
<213> ORGANISM: Homo Sapiens

<400> SEQUENCE: 10

Gln Val Gln Leu Val Glu Ser Gly Gly Val Val Gln Pro Gly Arg
1               5                   10                  15

Ser Arg Arg Leu Ser Cys Ala Ala Ser Gly Phe Thr Phe Ser Arg Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser Asn Lys Tyr Tyr Val Asp Ser Val
    50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg
```

-continued

```
<210> SEQ ID NO 11
<211> LENGTH: 98
<212> TYPE: PRT
<213> ORGANISM: Homo Sapiens

<400> SEQUENCE: 11

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Lys Tyr
 65                 70                  75                  80

Leu Gln Met Asn Ser Leu Arg Ala Glu Asp Thr Ala Val Tyr Tyr Cys
                85                  90                  95

Ala Arg
```

ANTI-ALPHA V IMMUNOLIPOSOME COMPOSITIONS, METHODS AND USES

CROSS-REFERENCE TO RELATED APPLICATION

This application is a divisional of U.S. application Ser. No. 12/118,994, filed May 12, 2008 now abandoned which claims priority to U.S. Provisional Application No. 60/917,397, filed 11 May 2007, the entire contents of which is incorporated herein by reference.

FIELD OF THE INVENTION

The subject matter described herein relates to a liposome composition having specific binding activity for alpha-V-integrin receptors. The composition is intended for use in treating conditions characterized by cells that express any alphav-comprising integrin, such as $\alpha v\beta 3$, $\alpha v\beta 5$, and $\alpha v\beta 6$ receptors.

BACKGROUND

Integrins are a superfamily of cell adhesion receptors, which exist as heterodimeric transmembrane glycoproteins. They are part of a large family of cell adhesion receptors which are involved in cell-extracellular matrix and cell-cell interactions. Integrins play critical roles in cell adhesion to the extracellular matrix (ECM) which, in turn, mediates cell survival, proliferation and migration through intracellular signaling. The receptors consist of two subunits that are non-covalently bound. Those subunits are called alpha ($\alpha$) and beta ($\beta$). The alpha subunits all have some homology to each other, as do the beta subunits. The receptors always contain one alpha chain and one beta chain and are thus called heterodimeric. Both of the subunits contribute to the binding of ligand. Eighteen alpha subunits and eight beta subunits have been identified, which heterodimerize to form at least 24 distinct integrin receptors.

Among the variety of alpha chain subunits is a protein chain referred to as alpha V. The ITGAV gene encodes integrin alpha chain V (vitronectin receptor, alpha-v; $\alpha v$, antigen CD51). The I-domain containing integrin alpha-v undergoes post-translational cleavage to yield disulfide-linked heavy and light chains, that combine with multiple integrin beta chains to form different integrins. Alternative splicing of the gene yields seven different transcripts; a, b, c, e, f, h, j altogether encoding six different protein isoforms of alphaV. Among the known associating beta chains (beta chains 1,3, 5,6, and 8; 'ITGB1', 'ITGB3', 'ITGB5', 'ITGB6', and 'ITGB8'), each can interact with extracellular matrix ligands. The alpha V beta 3 integrin, perhaps the most studied of these, is referred to as the vitronectin receptor (VNR). In addition to providing for cell attachment to other cells or to extracellular proteins such as vitronectin ($\alpha v\beta 3$) and fibronectin ($\alpha v\beta 6$), the integrins are capable of intracellular signaling which provides clues for cell migration and secretion of or elaboration of other proteins involved in cell motility and invasion and angiogenesis. The alpha-v integrin subfamily of integrins recognize the ligand motif arg-gly-asp (RGD) present in fibronection, vitronection, Von Willebrand factor, and fibrinogen. The alpha-V integrins are receptors for vitronectin, cytotactin, fibronectin, fibrinogen, laminin, matrix metalloproteinase-2, osteopontin, osteomodulin, prothrombin, thrombospondin and von Willebrand factor. In case of HIV-1 infection, the interaction with extracellular viral Tat protein seems to enhance angiogenesis in Kaposi's sarcoma lesions.

It has been established that integrins which are alpha-v containing heterodimers, particularly alpha-v/beta-6, the receptor for fibronectin, are involved in adhesion of carcinoma cells to fibronectin and vitronectin. This is especially true, for carcinoma cells arising from the malignant progression of colon cancer (Lehmann, M. et al., *Cancer Res.*, 54(8): 2102-7 (1994)). Furthermore, integrin expression in colon cancer cells is regulated by the cytoplasmic domain of the beta-6 integrin subunit which signals through the ERK2 pathway (Niu, J. et al., *Int. J. Cancer,* 99(4): 529-537 (2002)) and beta6 expression is associated with secretion of gelatinase B, an enzyme involved in tumor cell invasion and metastatic mechanisms (Agrez et al., *Int. J. Cancer,* 81(1):90-97 (1999)).

There is now considerable evidence that progressive tumor growth is dependent upon angiogenesis, the formation of new blood vessels, to provide tumors with nutrients and oxygen, to carry away waste products and to act as conduits for the metastasis of tumor cells to distant sites (Gastl, G. et al., *Oncol.,* 54(3):177-184 (1997)). Recent studies have further defined the roles of integrins in the angiogenic process. During angiogenesis, a number of integrins that are expressed on the surface of activated endothelial cells regulate critical adhesive interactions with a variety of ECM proteins to regulate distinct biological events such as cell migration, proliferation and differentiation. Specifically, the closely related but distinct integrins $\alpha v\beta 3$ and $\alpha v\beta 5$ have been shown to mediate independent pathways in the angiogenic process. An antibody generated against $\alpha v\beta 3$ blocked basic fibroblast growth factor (bFGF) induced angiogenesis, whereas an antibody specific to $\alpha v\beta 5$ inhibited vascular endothelial growth factor (VEGF) induced angiogenesis (Eliceiri et al., *J. Clin. Invest.,* 103:1227-1230 (1999); Friedlander et al., *Science,* 270:1500-1502 (1995)). Therefore, integrins, and especially the alpha V subunit containing integrins, are a therapeutic targets for diseases that involve angiogenesis, such as diseases of the eye and neoplastic diseases, tissue remodeling such as restenosis, and proliferation of certain cells types, particularly epithelial and squamous cell carcinomas.

Liposomes are spherical vesicles comprised of concentrically ordered lipid bilayers that encapsulate an aqueous phase. Liposomes serve as a delivery vehicle for therapeutic agents contained in the aqueous phase or in the lipid bilayers. Delivery of drugs in liposome-entrapped form can provide a variety of advantages, depending on the drug, including, for example, a decreased drug toxicity, altered pharmacokinetics, or improved drug solubility. Liposomes when formulated to include a surface coating of hydrophilic polymer chains, so-called Stealth® or long-circulating liposomes, offer the further advantage of a long blood circulation lifetime, due in part to reduced removal of the liposomes by the mononuclear phagocyte system. Often an extended lifetime is necessary in order for the liposomes to reach their desired target region or cell from the site of injection.

Targeted liposomes have targeting ligands or affinity moieties attached to the surface of the liposomes. The targeting ligands may be antibodies or fragments thereof, in which case the liposomes are referred to as immunoliposomes. When administered systemically targeted liposomes deliver the entrapped therapeutic agent to a target tissue, region or, cell. Because targeted liposomes are directed to a specific region or cell, healthy tissue is not exposed to the therapeutic agent. Such targeting ligands can be attached directly to the liposomes' surfaces by covalent coupling of the targeting ligand to the polar head group residues of liposomal lipid components (see, for example, U.S. Pat. No. 5,013,556). This approach, however, is suitable primarily for liposomes that lack surface-bound polymer chains, as the polymer chains interfere with interaction between the targeting ligand and its intended target (Klibanov, A. L., et al., *Biochim. Biophys. Acta.*, 1062:142-148 (1991); Hansen, C. B., et al., *Biochim. Biophys. Acta*, 1239:133-144 (1995)).

Alternatively, the targeting ligands can be attached to the free ends of the polymer chains forming the surface coat on the liposomes (Allen. T. M., et al., *Biochim. Biophys. Acta*, 1237:99-108 (1995); Blume, G. et al., *Biochim. Biophys. Acta*, 1149:180-184 (1993)). In this approach, the targeting ligand is exposed and readily available for interaction with the intended target.

The foregoing examples of the related art and limitations related therewith are intended to be illustrative and not exclusive. Other limitations of the related art will become apparent to those of skill in the art upon a reading of the specification and a study of the drawings.

SUMMARY OF THE INVENTION

The following aspects and embodiments thereof described and illustrated below are meant to be exemplary and illustrative, not limiting in scope.

Accordingly, in one aspect, an immunoliposome composition for targeting to a human alpha v integrin subunit is provided. In another aspect, an immunoliposome composition capable of specific binding to a cell expressing alpha V integrin is provided.

In one aspect, an alphaV-targeting immunoliposome composition comprised of liposomes bearing a targeting ligand which is an antibody-derived construct, such as an antibody fragment or derivative, for targeting to a human alpha v integrin subunit is provided.

In one embodiment of the alphaV-targeting immunoliposome composition of the invention, the targeting ligand is comprised of a heavy chain variable region derived from a parent antibody capable of specific binding to at least one of alphaVbeta1, alphaVbeta3, alphaVbeta5, alphaVbeta6, alphaVbeta8. In a specific embodiment the targeting ligand comprises the antibody heavy chain variable region residues 1-119 of SEQ ID NO: 1 comprising a framework-1 (FRI), complementarity determining region 1 (CDR1), FR2, CDR2, FR3, CDR3 and FR4 sequences. In one embodiment of the alphaV-targeting immunoliposome composition of the invention, the targeting ligand is comprised of a light chain variable region residues 1-108 of SEQ ID NO: 2 comprising FRI, CDR1, FR2, CDR2, FR3, CDR3 and FR4 sequences.

In still another aspect, of the alphaV-targeting immunoliposome composition of the invention, the targeting ligand is comprised of antibody heavy and light chain variable region having a sequence identified as SEQ ID NO: 1 residues 1-119 and SEQ ID NO: 2, residues 1-108.

In these various embodiment, the alphaV-targeting immunoliposome include an active entrapped in the liposomes, where 'entrapped' intends associated with the liposome lipid bilayer or with the internal aqueous compartments. The agent, in one embodiment, is a therapeutic agent, such as an antineoplastic agent. In a specific embodiment, the antineoplastic is a cytotoxic or cytostatic agent, such as doxorubicin. In another aspect, a method of treating a condition characterized by cells that express one or more of alphaVbeta1, alphaVbeta3, alphaVbeta5, alphaVbeta6, alphaVbeta8 is provided. The method includes administering an alphaV-targeting immunoliposome composition comprised of a targeting ligand comprising an antibody-derived construct as described above.

In another aspect, a method of treating a condition characterized by cells that express at least one of alphaVbeta1, alphaVbeta3, alphaVbeta5, alphaVbeta6, and alphaVbeta8 is provided. The method comprises administering immunoliposomes comprised of an isolated anti-alpha-V subunit monoclonal antibody, the antibody having at least one variable region having a sequence identified as SEQ ID NO: 1 residues 1-119 or SEQ ID NO: 2, residues 1-108.

In yet another aspect, the invention includes a method of treating a condition characterized by cells that express at least one of alphaVbeta1, alphaVbeta3, alphaVbeta5, alphaVbeta6, and alphaVbeta8, comprising administering immunoliposomes comprised of a targeting ligand comprising an antibody-derived construct as described above.

In still another aspect, the invention includes a method of treating a condition characterized by cells that express at least one of alphaVbeta1, alphaVbeta3, alphaVbeta5, alphaVbeta6, and alphaVbeta8, comprising administering the alphaV-targeting immunoliposome composition comprising a heavy chain variable region comprising FRI, CDRI, FR2, CDR2, FR3, CDR3 and FR4 sequences and a light chain variable region comprising FRI, CDRI, FR2, CDR2, FR3, CDR3 and FR4 sequences, wherein: (a) the heavy chain variable region CDR sequences are selected from those of SEQ ID NO: 1, and conservative modifications thereof; (b) the light chain variable region CDR sequences are selected from those of SEQ ID NO: 2, and conservative modifications thereof.

In a preferred embodiment, the methods find use in treating a neoplasm characterized by cells that express at least one of alphaVbeta1, alphaVbeta3, alphaVbeta5, alphaVbeta6, and alphaVbeta8.

In another aspect, a method for inhibiting the proliferation and/or growth of a cell expressing alpha V integrin, and/or inducing killing of a cell expressing alpha V integrin is provided, wherein cells are contacted with (e.g., administering to a subject) an alphaV-targeting immunoliposome composition.

Another aspect includes a therapeutic liposome composition sensitized to a target cell, comprising liposomes having an entrapped therapeutic agent, the liposomes including one or more targeting anti-alpha v antibodies in the form of a targeting conjugate. The targeting-ligand conjugate is comprised of (a) a lipid having a polar head group and a hydrophobic tail, (b) a hydrophilic polymer having a proximal end and a distal end, where the polymer is attached at its proximal end to the head group of the lipid, and (c) an anti-alpha V antibody-derived construct attached to the distal end of the polymer.

Also contemplated is a method of formulating a therapeutic liposome composition having sensitivity to a target cell. The method includes the steps of (i) providing a liposome formulation composed of pre-formed liposomes having an entrapped therapeutic agent; (ii) providing a targeting conjugate composed of (a) a lipid having a polar head group and a hydrophobic tail, (b) a hydrophilic polymer having a proximal end and a distal end, where the polymer is attached at its proximal end to the head group of the lipid, and (c) an anti-alpha V antibody targeting ligand attached to the distal end of the polymer; (iii) combining the liposome formulation and the targeting conjugate to form the therapeutic, target-cell sensitive liposome composition. In one embodiment, combining includes incubating under conditions effective to achieve insertion of the selected targeting conjugate into the liposomes of the selected liposome formulation.

In addition to the exemplary aspects and embodiments described above, further aspects and embodiments will become apparent by reference to the drawings and by study of the following descriptions.

BRIEF DESCRIPTION OF THE DRAWINGS

FIGS. 2A-2D are images, obtained using a confocal microscope, of A375S.2 cells incubated at 4° C. for 30 minutes with liposomes containing a fluorescent marker, where FIG. 2A-2B correspond to cells incubated with liposomes lacking a targeting ligand, and FIGS. 2C-2D are images of cells incubated with liposomes bearing alpha-integrin Fab targeting ligands (90:1 Fab: liposome);

FIGS. 3A-3H are images, obtained using a confocal microscope, of A375.S2 cells incubated at 37° C. for 10 minutes with liposomes containing a fluorescent marker, washed and incubated for 1 hours at 37° C., where the images correspond to untreated cells (FIGS. 3A-3B), cells treated with free doxorubicin (FIGS. 3C-3D), cells treated with liposomes lacking a targeting ligand (FIGS. 3E-3F), and cells incubated with liposomes bearing alpha-integrin Fab targeting ligands (90:1 Fab: liposome, FIGS. 3G-3H);

FIGS. 4A-4J are images, obtained using a confocal microscope, of A375.S2 cells incubated at 37° C. for 10 minutes with liposomes containing a fluorescent marker, washed and incubated for 0, 6, or 24 hours at 37° C., where the images correspond to untreated cells (FIGS. 4A-4B), cells treated with liposomes bearing alpha-integrin Fab targeting ligands (90:1 Fab: liposome) and incubated for 0 hours (FIGS. 4C-4D), 6 hours (FIGS. 4E-4F), 24 hours (FIGS. 4G-4H), or with liposomes lacking a targeting ligand (FIGS. 4I-4J; 24 hour post-wash incubation);

FIGS. 5A-5H are images, obtained using a confocal microscope, of B16-F10 cells incubated at 37° C. for 10 minutes with liposomes containing doxorubicin, washed and incubated for 1 hours at 37° C., where the images correspond to untreated cells (FIGS. 5A-5B), cells treated with free doxorubicin (FIGS. 5C-5D), cells treated with liposomes lacking a targeting ligand (FIGS. 5E-5F), and cells incubated with liposomes bearing alpha-integrin Fab targeting ligands (90:1 Fab: liposome, FIGS. 5G-5H);

FIGS. 6A-6C, * symbols), 180:1 (FIG. 6C, diamonds);

FIG. 7B, circles), and 90:1 (* symbols);

BRIEF DESCRIPTION OF THE SEQUENCES

Figure 1:
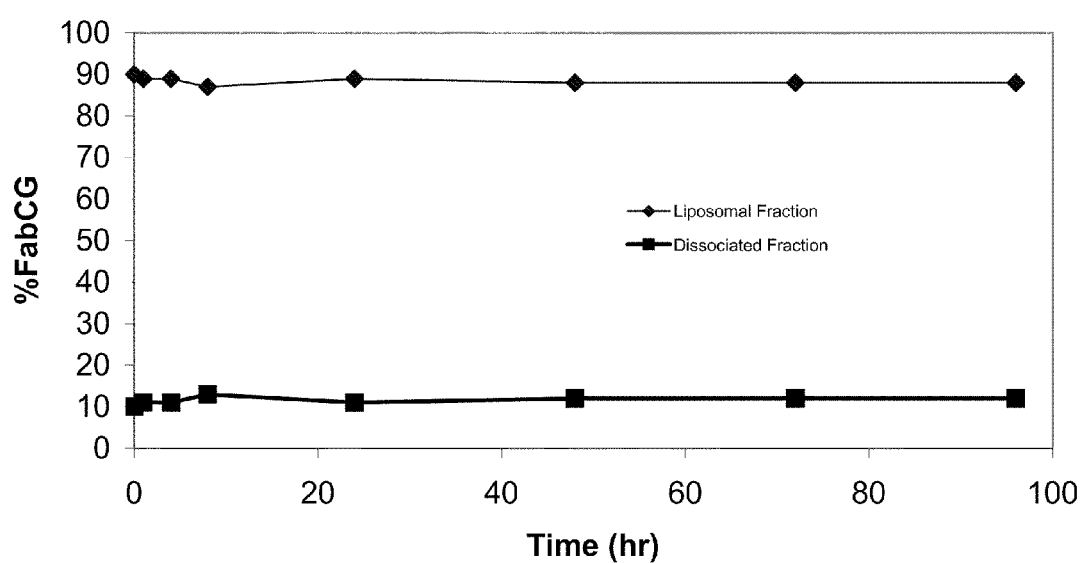
FIG. 1 is a graph of the percentage of Fab-PEG-DSPE conjugate remaining in the liposome (diamonds) and dissociated into human plasma (squares), as a function of incubation time, in hours, in human plasma.
Figure 6A:
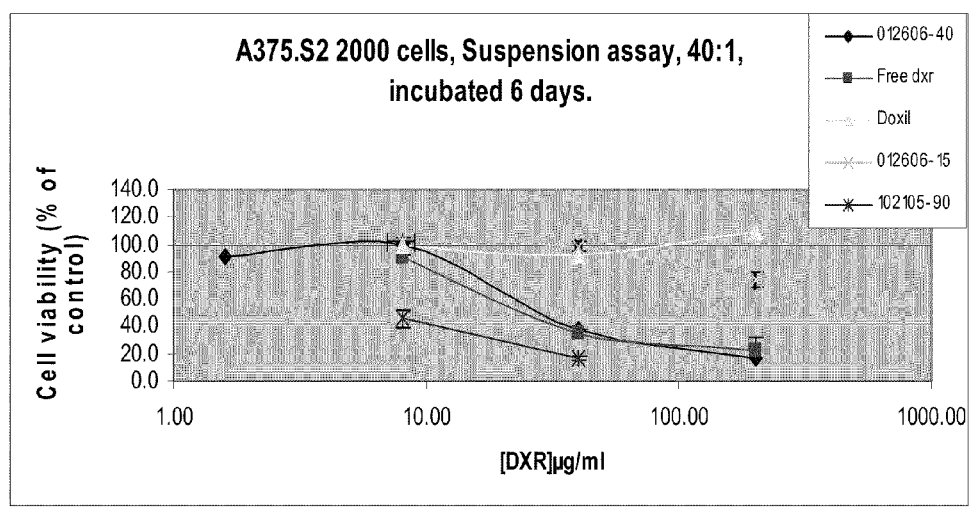
FIGS. 6A-6C are graphs showing the percent of viable A375.S2 cells, expressed as a percent of untreated control cells, as a function of doxorubicin concentration, in µg/mL, the doxorubicin in free form (squares), entrapped in liposomes lacking a targeting ligand (triangles), entrapped in liposomes bearing alpha-integrin Fab targeting ligands at Fab: liposome ratios of 15:1(x symbols), 40:1 (FIG. 6A, diamonds), 90:1 (FIG. 6B, diamonds.
Figure 6B:
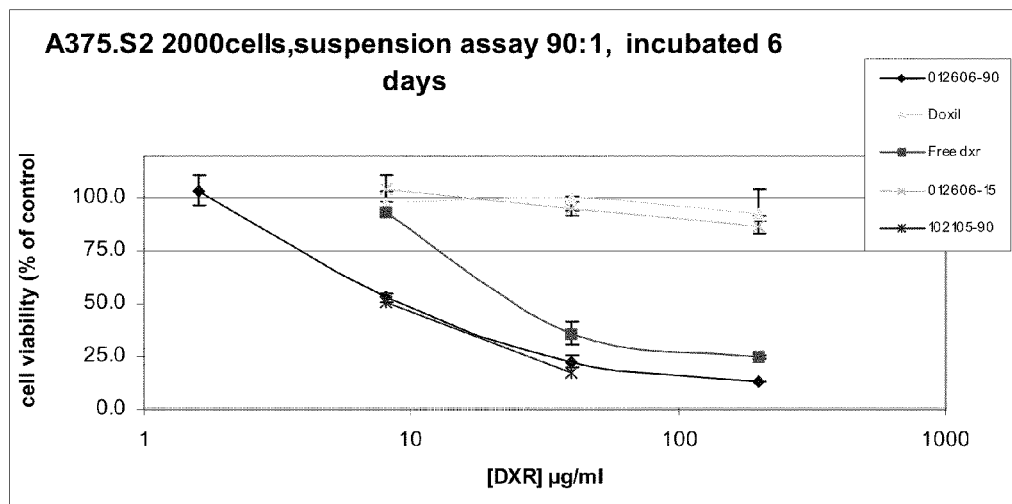
Figure 6C:
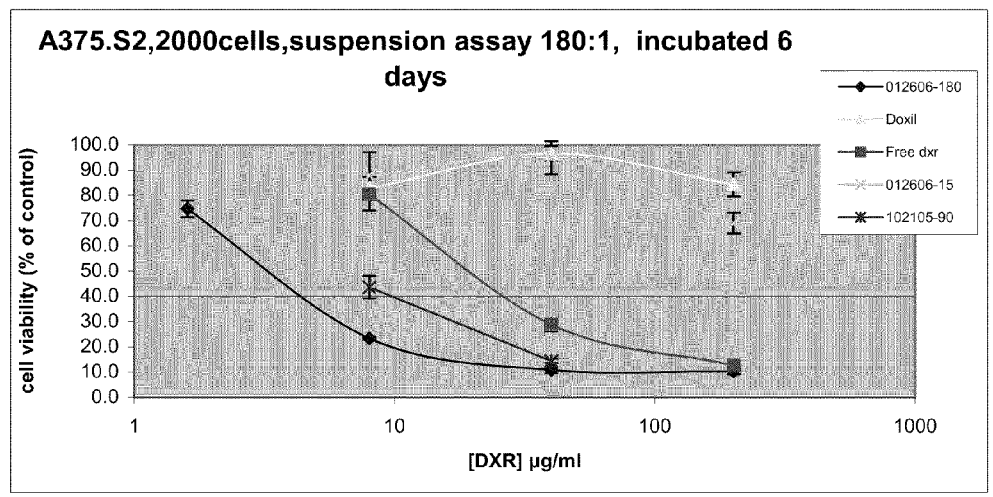
Figure 7A:
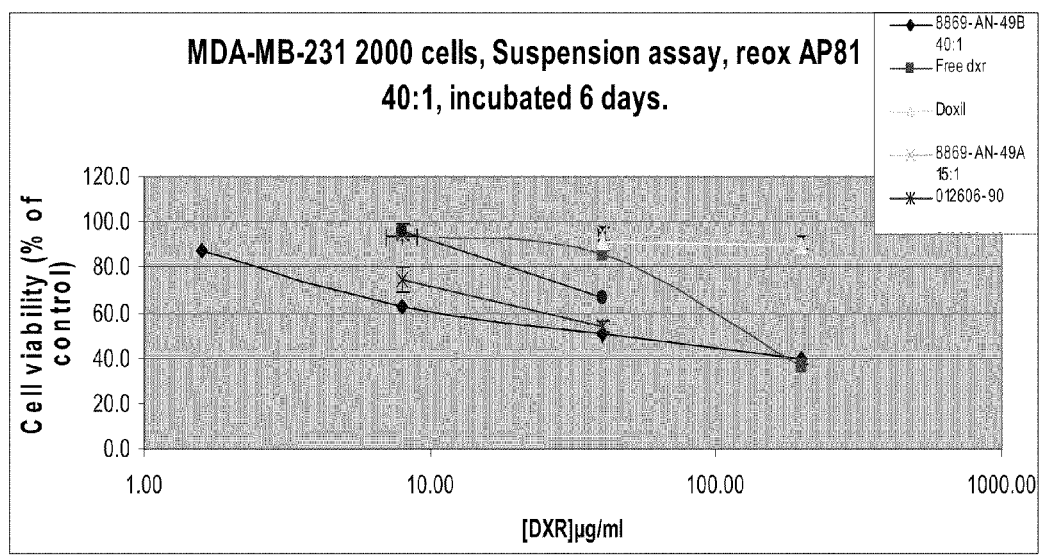
FIGS. 7A-7B are graphs showing the percent of viable MDA-MB-231 cells, expressed as a percent of untreated control cells, as a function of doxorubicin concentration, in µg/mL, the doxorubicin in free form (squares), entrapped in liposomes lacking a targeting ligand (triangles), entrapped in liposomes bearing alpha-integrin Fab targeting ligands at Fab: liposome ratios of 15:1(x symbols), 40:1 (FIG. 7A, diamonds.
Figure 7B:
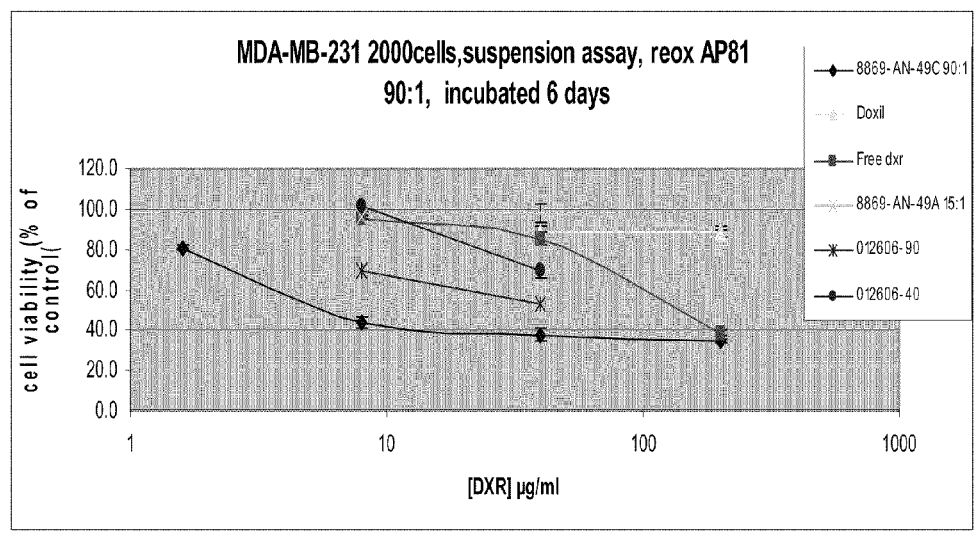
Figure 8:
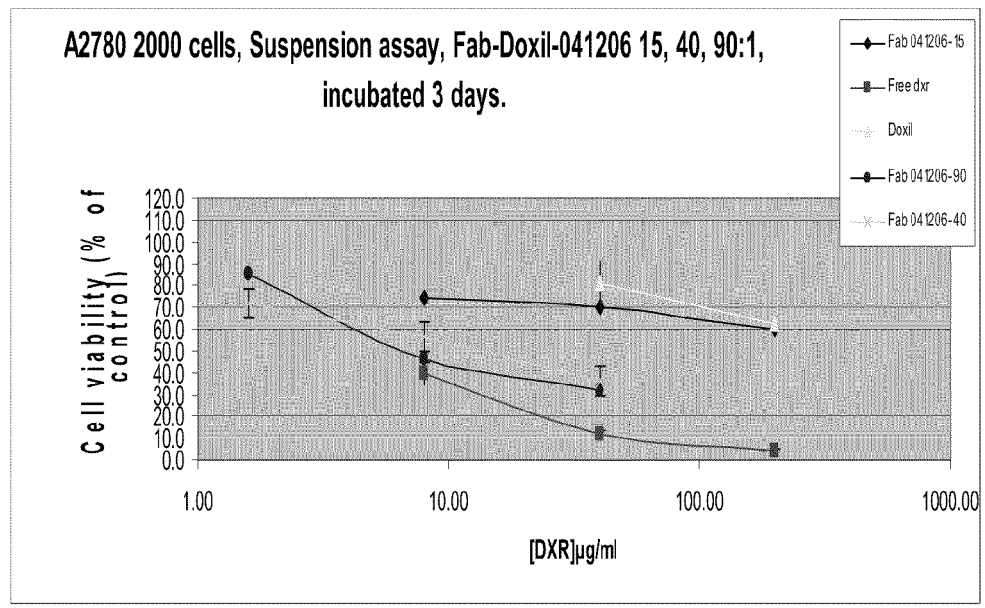
FIG. 8 is a graph showing the percent of viable A2780 cells, expressed as a percent of untreated control cells, as a function of doxorubicin concentration, in µg/mL, the doxorubicin in free form (squares), entrapped in liposomes lacking a targeting ligand (triangles), entrapped in liposomes bearing alpha-integrin Fab targeting ligands at Fab: liposome ratios of 15:1 (diamonds), 40:1 (* symbols), and 90:1 (circles)
Figure 9:
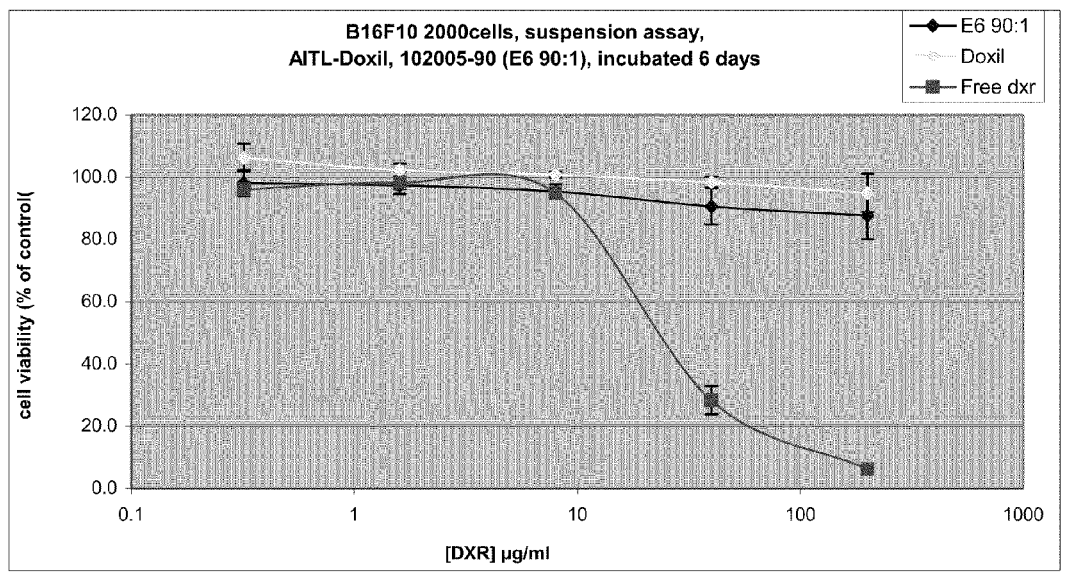
FIG. 9 is a graph showing the percent of viable B16-F10 cells, expressed as a percent of untreated control cells, as a function of doxorubicin concentration, in µg/mL, the doxorubicin in free form (squares), entrapped in liposomes lacking a targeting ligand (triangles), or entrapped in liposomes bearing alpha-integrin Fab targeting ligands at Fab: liposome ratios of 90:1 (diamonds)

| SEQ ID NO: | Description | Features |
|---|---|---|
| 1 | Parent antibody: heavy chain | |
| 2 | Parent antibody: light chain | |
| 3 | Secreted Fab heavy chain | |
| 4 | Single Chain antibody derived from parent antibody | |
| 5 | Nucleic acid construct for expression of scFv in E. coli | |

DETAILED DESCRIPTION

I. Definitions & Abbreviations

Abbreviations

CV column volume; Fv, antibody variable fragment consisting of VH and VL; scFv, single chain variable fragment; VH, variable heavy; VL, Variable light; PEG, Polyethylene Glycol; Gly4Cys, four glycine residues followed by a cysteine residue; His Tag, six histidine amino acid residues at the C-terminus of the protein; Fc, Fragment crystallizable Definitions The term "alpha v (αv) integrin", "alpha v subunit integrin", and "alpha v subunit containing integrin" are used interchangeably herein to mean alpha v transmembrane glycoprotein subunits of a functional integrin heterodimer and include all of the variants, isoforms and species homologs of alpha v. AlphaV polypeptides include one or more isoforms of proteins encoded by the ITGAV gene having names integrin, alpha V (vitronectin receptor, alpha polypeptide, antigen CD51); other aliases include, CD51, MSK8, VNRA; and other designations are integrin, alpha-V (vitronectin receptor, alpha polypeptide); antigen identified by monoclonal antibody L230; integrin alpha-V. The gene is located on human chromosome 2; location: 2q31-q32 (MIM: 193210; GeneID: 3685) The alphaV-comprising integrins bind a wide variety of ligands. Human antibodies of the invention may, in certain cases, cross-react with alpha v from species other than human, or other proteins that are structurally related to human alpha v (e.g., human alpha v homologs). In other cases, the antibodies may be completely specific for human alpha v and not exhibit species or other types of cross-reactivity.

As used herein, an "antibody" includes whole antibodies and any antigen binding fragment or single chain fragment thereof. Thus the antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, which can be incorporated into an antibody of the present invention. An "alpha v antibody", "alpha v subunit antibody" or "alpha v integrin antibody" is an antibody that specifically binds the alpha V subunit of an integrin. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian alpha-V subunit. Examples of binding fragments encompassed within the term "antigen binding portion" of an antibody include (i) a Fab fragment, a monovalent fragment consisting of the VL, VH, CL and CH, domains; (ii) a F(ab')$_2$ fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., Nature, 341:544-546 (1989)), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. Science, 242:423-426 (1988), Huston et al., Proc. Natl. Acad. Sci. USA, 85:5879-5883 (1988)). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH$_1$ domain and/or hinge region of the heavy chain. The various portions of antibodies can be joined together chemically by conventional techniques, or can be prepared as a contiguous protein using genetic engineering techniques.

A "complementarity determining region" or "CDR" refers to regions of somatic hypermutation of the immunoglobulin variable genes which occur after antigen stimulation during the differentiation of the B lymphocyte in the lymph glands leading to an amino acid sequence in the variable region of an antibody which impart the affinity and specificity of binding to the antibody; positioned at the end of several looped structures within the variable domain, CDRs form a surface that is "complementary to" the surface of an antigen or an epitope of that antigen.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Epitopes resulting from conformational folding of the integrin molecule which arise when amino acids from differing portions of the linear sequence of the integrin molecule come together in close proximity in three-dimensional space. Such conformational epitopes are distributed on the extracellular side of the plasma membrane. Conformational and nonconformational epitopes are distinguished in that the binding to the former but not the latter is lost in the presence of denaturing solvents.

A "framework region" or FR" refers to amino acid sequences which are found between complementarity determining regions (CDRs) in an antibody variable domain and are derived from the germline Heavy chain Variable (IGHV) genes (V, D, J genes) sequences of the human antibody genes.

Unless otherwise noted, the term "incubating" refers to conditions of time, temperature and liposome lipid composition which allow for penetration and entry of a selected component, such as a lipid or lipid conjugate, into the lipid bilayer of a liposome.

Unless otherwise noted, the term "pre-formed liposomes" refers to intact, previously formed unilamellar or multilamellar lipid vesicles.

Unless otherwise noted, the term "sensitized to a cell" or "target-cell sensitized" refers to a liposome that includes a ligand or affinity moiety covalently bound to the liposome and having binding affinity for alphaVbeta3 ($\alpha v \beta 3$) and alphaVbeta5 ($\alpha v \beta 5$) receptor expressed or other alphaV subunit-containing integrins on a cell.

Unless otherwise noted, the term "therapeutic liposome composition" refers to liposomes that include a therapeutic agent entrapped in the aqueous spaces of the liposomes or in the lipid bilayers of the liposomes.

Unless otherwise noted, the term "vesicle-forming lipid" refers to any lipid capable of forming part of a stable micelle or liposome composition and typically including one or two hydrophobic, hydrocarbon chains or a steroid group and may contain a chemically reactive group, such as an amine, acid, ester, aldehyde or alcohol, at its polar head group.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. Thus as used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. Human germline antibody consensus sequences for various regions and domains of human antibodies; FR1, FR2, FR3, FR4, CH1, hinge1, hinge2, hinge3, hinge4, CH2, CH3 or fragment thereof are described in Table 2 of, and optionally with at least one substitution, insertion or deletion as provided in FIGS. 1-42 of, PCT WO05/005604 and U.S. Ser. No. 10/872,932 each entirely incorporated herein by reference. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than ten amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A monoclonal antibody from a non-human animal, such as a mouse, rat, baboon, or rabbit, may also be used as a parent antibody providing a source of the alphaV binding regions of the antibody-derived targeting-ligand.

The terms "monoclonal antibody" or "parental antibody" as used herein refer to a preparation of antibody molecules of single molecular composition. A monoclonal antibody displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

An "isolated antibody," as used herein, is intended to refer to an antibody which is substantially free of other antibodies having different antigenic specificities (e.g., an isolated antibody that specifically binds to alpha V is substantially free of antibodies that specifically bind antigens other than alpha V). An isolated antibody that specifically binds to an epitope, isoform or variant of human alpha V may, however, have cross-reactivity to other related antigens, e.g., from other species (e.g., alpha V species homologs). Moreover, an isolated antibody may be substantially free of other cellular material and/or chemicals.

As used herein, "specific binding" refers to antibody binding to a predetermined antigen. Typically, the parental antibody binds with a dissociation constant ($K_D$) of $10^{-7}$ M or less, and binds to the predetermined antigen with a $K_D$ that is at least twofold less than its $K_D$ for binding to a non-specific antigen (e.g., BSA, casein) other than the predetermined antigen or a closely-related antigen.

The phrases "an antibody recognizing an antigen" and "an antibody specific for an antigen" are used interchangeably herein with the term "an antibody which binds specifically to an antigen".

As used herein, $K_D$ refers to the dissociation constant, specifically, the antibody $K_D$ for a predetermined antigen, and is a measure of affinity of the antibody for a specific target. High affinity antibodies have a $K_D$ of $10^{-8}$ M or less, more preferably $10^{-9}$ M or less and even more preferably $10^{-10}$ M or less, for a predetermined antigen. The reciprocal of $K_D$ is $K_A$, the association constant. The term "$k_{dis}$" or "$k_2$", or "$k_d$", is intended to refer to the dissociation rate of a particular antibody-antigen interaction. The "$K_D$", is the ratio of the rate of dissociation ($k_2$), also called the "off-rate ($k_{off}$)", to the rate of association rate ($k_1$) or "on-rate ($k_{on}$)". Thus, $K_D$ equals $k_2/k_1$ or $k_{off}/k_{on}$ and is expressed as a molar concentration (M). It follows that the smaller the $K_D$, the stronger the binding. So a $K_D$ of $10^{-6}$ M (or 1 microM) indicates weak binding compared to $10^{-9}$ M (or 1 nM).

II. Immunoliposome Composition

In one aspect, an immunoliposome composition is provided, the composition comprised of liposomes that include as a targeting ligand an antibody-derived protein which is a monomeric, dimeric or multimeric construct, having binding specificity for an αv-comprising integrin on the surface of a cell. The alpha V targeting-ligand is incorporated into the liposomes in the form of a lipid-polymer-protein conjugate, also referred to herein as a lipid-polymer-ligand conjugate. As will be described below, the antibody-derived construct has specific affinity for αv-integrin receptors, and targets the liposomes to cells that express any of the alphaV-comprising intergrin heterodimers including but not limited to αvβ3, αvβ5 and αvβ6 receptors. The following sections describe the liposome components, including the liposome lipids and therapeutic agents, preparation of liposomes bearing an anti-alpha v targeting ligand, and methods of using the liposomal composition for treatment of disorders characterized by cellular expression of alphaV-integrins such as αvβ3, αvβ5, and αvβ6 integrin receptors.

A. Liposome Lipid Components

Liposomes suitable for use in the composition of the present invention include those composed primarily of vesicle-forming lipids. Such a vesicle-forming lipid is one which can form spontaneously into bilayer vesicles in water, as exemplified by the phospholipids, with its hydrophobic moiety in contact with the interior, hydrophobic region of the bilayer membrane, and its head group moiety oriented toward the exterior, polar surface of the membrane. Lipids capable of stable incorporation into lipid bilayers, such as cholesterol and its various analogs, can also be used in the liposomes.

The vesicle-forming lipids are preferably lipids having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation. The above-described lipids and phospholipids whose carbon chains have varying degrees of saturation can be obtained commercially or prepared according to published methods. Other suitable lipids include glycolipids, cerebrosides and sterols, such as cholesterol.

Cationic lipids are also suitable for use in the liposomes of the invention, where the cationic lipid can be included as a minor component of the lipid composition or as a major or sole component. Such cationic lipids typically have a lipophilic moiety, such as a sterol, an acyl or diacyl chain, and where the lipid has an overall net positive charge. Preferably, the head group of the lipid carries the positive charge. Exemplary cationic lipids include 1,2-dioleyloxy-3-(trimethylamino)propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]N,N,N-trimethylammonium chloride (DOTMA); 3[N—(N',N'-dimethylaminoethane)carbamoly] cholesterol (DC-Chol); and dimethyldioctadecylammonium (DDAB). The cationic vesicle-forming lipid may also be a neutral lipid, such as dioleoylphosphatidyl ethanolamine (DOPE) or an amphipathic lipid, such as a phospholipid, derivatized with a cationic lipid, such as polylysine or other polyamine lipids. For example, the neutral lipid (DOPE) can be derivatized with polylysine to form a cationic lipid.

The vesicle-forming lipid can be selected to achieve a specified degree of fluidity or rigidity, to control the stability of the liposome in serum, to control the conditions effective for insertion of the targeting conjugate, as will be described, and/or to control the rate of release of the entrapped agent in the liposome. Liposomes having a more rigid lipid bilayer, or a liquid crystalline bilayer, are achieved by incorporation of a relatively rigid lipid, e.g., a lipid having a relatively high phase transition temperature, e.g., up to 60° C. Rigid, i.e., saturated, lipids contribute to greater membrane rigidity in the lipid bilayer. Other lipid components, such as cholesterol, are also known to contribute to membrane rigidity in lipid bilayer structures.

On the other hand, lipid fluidity is achieved by incorporation of a relatively fluid lipid, typically one having a lipid phase with a relatively low liquid to liquid-crystalline phase transition temperature, e.g., at or below room temperature.

The liposomes also include a vesicle-forming lipid derivatized with a hydrophilic polymer. As has been described, for example in U.S. Pat. No. 5,013,556, including such a derivatized lipid in the liposome composition forms a surface coating of hydrophilic polymer chains around the liposome. The surface coating of hydrophilic polymer chains is effective to increase the in vivo blood circulation lifetime of the liposomes when compared to liposomes lacking such a coating.

Vesicle-forming lipids suitable for derivatization with a hydrophilic polymer include any of those lipids listed above, and, in particular phospholipids, such as distearoyl phosphatidylethanolamine (DSPE).

Hydrophilic polymers suitable for derivatization with a vesicle-forming lipid include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences. The polymers may be employed as homopolymers or as block or random copolymers.

A preferred hydrophilic polymer chain is polyethyleneglycol (PEG), preferably as a PEG chain having a molecular weight between 500-10,000 daltons, more preferably between 750-10,000 daltons, still more preferably between 750-5000 daltons. Methoxy or ethoxy-capped analogues of PEG are also preferred hydrophilic polymers, commercially available in a variety of polymer sizes, e.g., 120-20,000 Daltons.

Preparation of vesicle-forming lipids derivatized with hydrophilic polymers has been described, for example in U.S. Pat. No. 5,395,619. Preparation of liposomes including such derivatized lipids has also been described, where typically between 1-20 mole percent of such a derivatized lipid is included in the liposome formulation (see, for example, U.S. Pat. No. 5,013,556).

B. Anti-Alpha-V Targeting Ligand

The antibody derived targeting ligand of the invention, as defined herein, to be used to prepare the liposomal compositions of the present invention, may be derived from any anti-alpha V specific antibody or selected from a library of pre-formed antibody-derived structures, e.g. a phage library comprising antibody Fab' or scFv or Fv. In one embodiment, the antibody for use in the liposome composition described herein comprises antigen binding domains derived from a human anti-alpha V antibody generated by immunization of a transgenic mouse containing genes for the expression of human immunoglobulins. Preparation of a parent anti-alpha V antibody known as CNTO 95, from which the antigen binding domains are derived is described in Preparation of the antibody is described in detail in PCT publication no. WO 02/12501 and U.S. Pat. No. 7,163,681 both incorporated by reference herein.

The antibody-derived targeting ligand includes any protein or peptide containing molecule that comprises at least a portion of a complementarity determining region (CDR) of a heavy or light chain or a ligand binding portion thereof derived from the antibody designated "CNTO 95" (see PCT publication no. WO 02/12501 and U.S. Publication No. 2003/040044), in combination with a heavy chain or light chain variable region, a heavy chain or light chain constant region, a framework region, or any portion thereof, that can be incorporated into an antibody.

Preferably, the CDR 1, 2, and/or 3 of the engineered targeting ligand described above comprise the exact amino acid sequence(s) as those of the fully human Mab designated CNTO 95, Gen0101, CNTO 95, C371A generated by immunization of a transgenic mouse as disclosed herein. However, the ordinarily skilled artisan will appreciate that some deviation from the exact CDR sequences of CNTO 95 may be possible while still retaining the ability of the antibody to bind Alpha V effectively (e.g., conservative substitutions). In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 (as shown in SEQ ID NO: 1). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (as shown in SEQ ID NO: 2) of the light chain of CNTO95. In a preferred embodiment the three heavy chain CDRs and the three light chain CDRs of the anitbody or antigen-binding fragment have the amino acid sequence of the corresponding CDR of mAb CNTO 95 (as shown in SEQ ID Nos: 1 and 2). Accordingly, in another embodiment, the engineered antibody may be composed of one or more CDRs that are, for example, 90%, 95%, 98% or 99.5% identical to one or more CDRs of CNTO 95. Anti-alpha-V subunit antibodies of the present invention can include, but are not limited to, at least one portion, sequence or combination selected from 5 to all of the contiguous amino acids of at least one of six CDRs shown in SEQ ID NOS: 1 and 2. An anti-alpha-V subunit antibody can further optionally comprise a polypeptide of at least one of 70-100% of the contiguous amino acids of at least one of SEQ ID NOS: 1 and 2. For example, the amino acid sequence of a light chain variable region can be compared with the sequence of SEQ ID NO: 2, residues 1-108, or the amino acid sequence of a heavy chain CDR3 can be compared with SEQ ID NO: 1, residues 1-119.

As disclosed and claimed herein, the sequences set forth in SEQ ID NOs. 1-4 include "conservative sequence modifications", i.e. amino acid sequence modifications which do not significantly affect or alter the binding characteristics of the antibody encoded by the nucleotide sequence or containing the amino acid sequence. Such conservative sequence modifications include amino acid substitutions, additions and deletions. Modifications can be introduced into SEQ ID NOs: 1-2 or to the nucleic acids encoding them by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-Alpha V antibody is preferably replaced with another amino acid residue from the same side chain family.

In another aspect of the invention, the structural features of a human anti-alpha V antibody are used to create structurally related a human anti-alpha V targeting ligand that retain ability to bind to alphaV. More specifically, one or more antigen binding regions, specifically the variable regions and the CDR regions of the anti-alpha V antibody can be combined recombinantly with other known human constant regions or framework regions and CDRs to create additional, recombinantly-engineered, human anti-alpha V targeting moieties of the invention.

At least one antibody of the invention binds at least one specified epitope specific to at least one alphaV subunit protein, subunit, fragment, portion or any combination thereof. The at least one epitope can comprise at least one portion of said protein, preferably comprised of at least one extracellular, soluble, external or cytoplasmic portion of said protein. The at least one specified epitope can comprise any combination of at least one amino acid sequence of at least 1-3 amino acids to the entire specified portion of contiguous amino acids of a protein encoded by the ITGAV gene (Gene ID: 3683).

Amino acids in an anti-alpha-V antibody to be used in the present invention that are essential for function can be identified by methods known in the art, such as site-directed mutagenesis or alanine-scanning mutagenesis (e.g., Ausubel, supra, Chapters 8, 15; Cunningham and Wells, Science 244: 1081-1085 (1989)). The latter procedure introduces single alanine mutations at every residue in the molecule. The resulting mutant molecules are then tested for biological activity, such as, but not limited to at least one alpha-V subunit neutralizing activity. Sites that are critical for antibody binding can also be identified by structural analysis such as crystallization, nuclear magnetic resonance or photoaffinity labeling (Smith, et al., *J. Mol. Biol.* 224:899-904 (1992) and de Vos, et al., *Science* 255:306-312 (1992)).

The present invention is not limited to the use of CNTO 95 mAb, its variable domains, or CDR sequences. It is anticipated that any appropriate anti-alphaV antibody and corresponding anti-αv CDRs described in the art may be substituted therefor. Other anti-αv subunit antibodies may be developed by screening hybridomas, combinatorial libraries, or specific antibody phage display libraries [W. D. Huse et al., 1988, *Science*, 246:1275-1281] for binding to a human αV-containing integrin epitope. A collection of antibodies, including hybridoma products or antibodies derived from any species immunoglobulin repertoire may be screened in a conventional competition assay, with one or more of the known anti-alphaV antibodies described herein. Thus, the invention may provide an antibody, other than CNTO95 derived antibodies, which is capable of binding to the αv-containing receptors.

In another embodiment, the anti-alphaV antibody may be 17E6, a fragment, or variant thereof based on the binding domains of 17E6 as described in U.S. Pat. No. 5,985,278 which reacts with the αV-chain of human αV-integrins, blocking the attachment to the integrin substrate of the αV-integrin bearing cell, triggering reversal of established cell matrix interaction caused by αV-integrins, blocking tumor development, and showing no cytotoxic activity. In yet another embodiment, the anti-alpha V antibody may be murine monoclonal B9 and the humanized antibody HuB9 as described in U.S. Pat. No. 6,160,099 which react with the αV-chain of human $\alpha_v\beta_3$ and $\alpha_v\beta_5$ integrins.

Variations derived from the naturally occurring antibody structure, as defined herein which are particularly useful in the present invention include Fabs and scFv. ScFv (single-chain variable fragment antibody) is a minimal antibody moiety in which the variable regions from the heavy and light chains (Vh and Vl) of immunoglobulin are joined by a flexible linker (U.S. Pat. No. 5,260,203). The resulting linked domains represent a variable region fragment, which retains both affinity and specificity of the parent antibody. These small antibody fragments can be produced in *E. coli* providing a fast and economic manufacturing option. A scFv of CNTO95 was developed as a targeting moiety to specifically direct drug containing STEALTH® Liposomes to aVb3 and aVb5 integrins which are known to be present on numerous types of cancer cells as well as angiogenic endothelial cells thereby representing an ideal targeting opportunity for drug delivery to subjects with neoplastic disease. One particular advantage of the scFv is that, in contrast to larger antibody fragments, a scFv contains only 4 cysteine residues and these are engaged in the 2 disulfide bonds of the V-domains. This facilitates introduction of a free cysteine residue for chemical conjugation. Moreover, the small size of the scFv is less likely to impact the stability and low non-specific interactions of STEALTH® Liposomes. A further advantage of an scFv with the alpha V targeting properties of CNTO95 are the ability to cause receptor internalization upon binding. Certain specific embodiments of the anti-alphaV targeting antibody constructs are single chain binding fragments (scFv) which may be prepared from a parent antibody as described in Example 11 and as exemplified by SEQ ID NO: 4.

In another embodiment the targeting antibody is a Fab, which represents a monovalent binding fragment of an antibody, comprising both heavy chain and light chain portions of an antibody, which may be produced by cleavage from an antibody or be synthesized recombinantly and expressed as the heterodimeric structure. In the present invention, exemplary forms of Fabs produced by both processes are described in Example 2 and 9. A Fab derived from cleavage of the parent CNTO95 IgG comprising the full-length heavy and light chains of the antibody (SEQ ID NO: 1 and 2, respectively) cleaved by pepsin is represented by residues 1-234 or SEQ ID NO: 1 and the full-length light chain (SEQ ID NO: 2). A recombinantly engineered host cell line expressing and secreting a Fab (sFab) which is represented by SEQ ID NO: 3 and SEQ ID NO: 2 is particularly useful for the purposes of conjugation and insertion into a pre-formed liposome among other uses.

It is useful for the targeting antibody of the present invention to comprise a predetermined site for conjugation to a chemically moiety capable of insertion into the lipid structure of the liposome. While chemical modification of and addition of reactive groups is possible by standard techniques, it is convenient to genetically encode such a site into the structure of the antibody whenever possible. In the case of the recombinantly expressed and secreted antibody targeting constructs, including the sFab and scFv antibody constructs, each polypeptide chain has an additional C-terminal tail amino acid sequence having a means for chemically modifying the polypeptide such as through a free sulfhydryl of a cysteine side chain or an amine residue of a lysine sidechain. Exemplary methods of incorporating a predetermined site for conjugation are taught in e.g. U.S. Pat. No. 5,837,846 which is incorporated herein by reference and which embodiments include a C-terminal cysteine or a C-terminal tail peptide bonded to the C-terminus of the antibody heavy chain or heavy chain fragment or scFv and, optionally, having an amino acid sequence selected from the group consisting of Ser-Cys, $(Gly)_4$-Cys, and $(His)_6$-$(Gly)_4$-Cys thereby incorporating linking means as well as purification means (his-tag).

C. Preparation of Lipid-Polymer-Antibody Conjugate

The anti-alpha V antibody is covalently attached to the free distal end of a hydrophilic polymer chain, which is attached at its proximal end to a vesicle-forming lipid. There are a wide variety of techniques for attaching a selected hydrophilic polymer to a selected lipid and activating the free, unattached end of the polymer for reaction with a selected ligand, and in particular, the hydrophilic polymer polyethyleneglycol (PEG) has been widely studied (Allen, T. M., et al., *Biochemicia et Biophysica Acta*, 1237:99-108 (1995); Zalipsky, S., *Bioconjugate Chem.*, 4(4):296-299 (1993); Zalipsky, S., et al. *FEBS Lett.*, 353:71-74 (1994); Zalipsky, S. et al., *Bioconjugate Chemistry*, 6(6):705-708 (1995); Zalipsky, S., in STEALTH LIPOSOMES (D. Lasic and F. Martin, Eds.) Chapter 9, CRC Press, Boca Raton, Fla. (1995)).

Generally, the PEG chains are functionalized to contain reactive groups suitable for coupling with, for example, sulfhydryls, amino groups, and aldehydes or ketones (typically derived from mild oxidation of carbohydrate portions of an antibody) present in a wide variety of ligands. Examples of such PEG-terminal reactive groups include maleimide (for reaction with sulfhydryl groups), N-hydroxysuccinimide (NHS) or NHS-carbonate ester (for reaction with primary amines), hydrazide or hydrazine (for reaction with aldehydes or ketones), iodoacetyl (preferentially reactive with sulfhydryl groups) and dithiopyridine (thiol-reactive). Synthetic reaction schemes for activating PEG with such groups are set forth in U.S. Pat. Nos. 5,631,018, 5,527,528, 5,395,619, and the relevant sections describing synthetic reaction procedures are expressly incorporated herein by reference.

In supporting studies, the anti-integrin antibody fragment was a Fab' antibody produced by enzymatic cleavage of a full length parent antibody, which was attached to a lipid-PEG conjugate, as described in Example 2. In brief, a lipopolymer with a reactive end, maleimide-PEG-DSPE, was inserted into drug loaded liposomes, for subsequence conjugation between the reactive PEG end and the Fab' targeting ligand. The Fab' was prepared by first reducing F(ab')$_2$ to cleave solvent accessible disulfide bonds and then reoxidizing the protein in a controlled manner to selectively reform the disulfide bonds between the heavy and light chains, thus forming Fab' at a high purity. The reoxidized Fab' was then added to the liposomes bearing reactive maleimide groups to conjugate the Fab' ligand to the external surface of the liposomes.

In another study, as described in Example 9, the anti-alphaV antibody-derived construct was also a Fab' fragment but was a variant of the parental sequence (SEQ ID NO: 3) synthesized by recombinant methods and conjugated to a PEGylated-lipid for surface insertion into a pre-formed liposome.

In another study, as described in Example 11, the anti-alphaV antibody-derived construct was a scFv which was a produced variant of the parental sequence heavy chain (SEQ ID NO: 1) variable domain with the parental sequence light chain (SEQ ID NO: 2) variable domain with a flexible polypeptide linker interposed therebetween. The construct was produced by linking coding sequences for the variable domains operably with a coding sequence for the linking a sequence by recombinant methods. The expressed purified scFv, which retained binding specificity for alphaV-integrins was conjugated to a PEGylated-lipid for surface insertion into a pre-formed liposome.

D. Liposome Preparation

Various approaches have been described for preparing liposomes having a targeting ligand attached to the distal end of liposome-attached polymer chains. One approach involves preparation of lipid vesicles which include an end-functionalized lipid-polymer derivative; that is, a lipid-polymer conjugate where the free polymer end is reactive or "activated" (see, for example, U.S. Pat. Nos. 6,326,353 and 6,132,763). Such an activated conjugate is included in the liposome composition and the activated polymer ends are reacted with a targeting ligand after liposome formation. Example 2 describes preparation of liposomes using this approach.

In another approach, the lipid-polymer-ligand conjugate is included in the lipid composition at the time of liposome formation (see, for example, U.S. Pat. Nos. 6,224,903, 5,620,689).

In another method of preparing a targeted liposome, a micellar solution of the lipid-polymer-ligand conjugate is incubated with a suspension of liposomes and the lipid-polymer-ligand conjugate is inserted into the pre-formed liposomes (see, for example, U.S. Pat. Nos. 6,056,973 and 6,316,024). Examples 3, 9 and 11 describe preparation of liposomes using this approach.

It will be appreciated that liposomes carrying an entrapped agent and bearing surface-bound targeting ligands, i.e., targeted, therapeutic liposomes, are prepared by any of these approaches. A preferred method of preparation is the insertion method, where pre-formed liposomes and are incubated with the targeting conjugate to achieve insertion of the targeting conjugate into the liposomal bilayers. In this approach, liposomes are prepared by a variety of techniques, such as those detailed in Szoka, F., Jr., et al., *Ann. Rev. Biophys. Bioeng.*, 9:467 (1980), and specific examples of liposomes prepared in support of the present invention will be described below. Typically, the liposomes are multilamellar vesicles (MLVs), which can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

The liposomes can include a vesicle-forming lipid derivatized with a hydrophilic polymer to form a surface coating of hydrophilic polymer chains on the liposomes surface. Addition of a lipid-polymer conjugate is optional, since after the insertion step the liposomes will include lipid-polymer-targeting ligand. Additional polymer chains added to the lipid mixture at the time of liposome formation and in the form of a lipid-polymer conjugate result in polymer chains extending from both the inner and outer surfaces of the liposomal lipid bilayers. Addition of a lipid-polymer conjugate at the time of liposome formation is typically achieved by including between 1-20 mole percent of the polymer-derivatized lipid with the remaining liposome forming components, e.g., vesicle-forming lipids. Exemplary methods of preparing polymer-derivatized lipids and of forming polymer-coated liposomes have been described in U.S. Pat. Nos. 5,013,556, 5,631,018 and 5,395,619, which are incorporated herein by reference. It will be appreciated that the hydrophilic polymer may be stably coupled to the lipid, or coupled through an unstable linkage, which allows the coated liposomes to shed the coating of polymer chains as they circulate in the bloodstream or in response to a stimulus.

The liposomes also include a therapeutic or diagnostic agent, and exemplary agents are provided below. The selected agent is incorporated into liposomes by standard methods, including (i) passive entrapment of a water-soluble compound by hydrating a lipid film with an aqueous solution of the agent, (ii) passive entrapment of a lipophilic compound by hydrating a lipid film containing the agent, and (iii) loading an ionizable drug against an inside/outside or outside/inside liposome chemical or pH gradient. Other methods, such as reverse-phase evaporation, are also suitable.

After liposome formation, the liposomes can be sized to obtain a population of liposomes having a substantially homogeneous size range, typically between about 0.01 to 0.5 microns, more preferably between 0.03-0.40 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, F. J., in SPECIALIZED DRUG DELIVERY SYSTEMS—MANUFACTURING AND PRODUCTION TECHNOLOGY, P. Tyle, Ed., Marcel Dekker, New York, pp. 267-316 (1990)).

In one embodiment, after formation of the liposomes, a targeting ligand is incorporated to achieve a target-cell sensitized, therapeutic liposome. The targeting ligand can be incorporated attaching the ligand to an activated end on the hydrophilic polymer chain (Example 2) or by incubating the pre-formed liposomes with the lipid-polymer-ligand conjugate (Examples 3, 9, and 11). In the latter approach, the pre-formed liposomes and the conjugate are incubated under conditions effective to achieve insertion of the conjugate into the liposome bilayer. More specifically, the two components are incubated together under conditions which achieve insertion of the conjugate in such a way that the targeting ligand is oriented outwardly from the liposome surface, and therefore available for interaction with its cognate receptor. It will be appreciated that the conditions effective to achieve insertion of the targeting conjugate into the liposome are determined based on several variables, including, the desired rate of insertion, where a higher incubation temperature may achieve a faster rate of insertion, the temperature to which the ligand can be safely heated without affecting its activity, and to a lesser degree the phase transition temperature of the lipids and the lipid composition. It will also be appreciated that insertion can be varied by the presence of solvents, such as amphipathic solvents including polyethyleneglycol and ethanol, or detergents.

The targeting conjugate, in the form of a lipid-polymer-ligand conjugate, will typically form a solution of micelles when the conjugate is mixed with an aqueous solvent. The micellar solution of the conjugates is mixed with a suspension of pre-formed liposomes for insertion of the conjugate into the liposomal lipid bilayers. Accordingly, in another aspect, a plurality of targeting conjugates, such as a micellar solution of targeting conjugates, for use in preparing a targeted, therapeutic liposome composition, is contemplated. Each conjugate is composed of (i) a lipid having a polar head group and a hydrophobic tail, (ii) a hydrophilic polymer having a proximal end and a distal end, where the polymer is attached at its proximal end to the head group of the lipid, and (iii) an anti-alpha V antibody targeting ligand attached to the distal end of the polymer.

Also contemplated is a method of formulating a therapeutic liposome composition having sensitivity to a target cell. The method includes the steps of (i) providing a liposome formulation composed of pre-formed liposomes having an entrapped therapeutic agent; (ii) providing a targeting conjugate composed of (a) a lipid having a polar head group and a hydrophobic tail, (b) a hydrophilic polymer having a proximal end and a distal end, where the polymer is attached at its proximal end to the head group of the lipid, and (c) an anti-alpha V antibody targeting ligand attached to the distal end of the polymer; (iii) combining the liposome formulation and the targeting conjugate to form the therapeutic, target-cell sensitive liposome composition. In one embodiment, combining includes incubating under conditions effective to achieve insertion of the selected targeting conjugate into the liposomes of the selected liposome formulation.

Exemplary Immunoliposomes

In supporting studies, immunoliposomes having an anti-αv integrin Fab antibody were prepared as described in Example 1 and 2 and with an alternative embodiment of a Fab secreted by an engineered host cell, in Example 9. In another embodiment, immunoliposomes having an anti-αv integrin scFv targeting moiety were prepared as described in Example 12. In brief, liposomes were prepared from the lipids HSPC, cholesterol. The therapeutic agent doxorubicin was loaded into the liposomes by remote loading against an ammonium ion gradient (Doxil®). In one method of attaching the targeting moiety to the liposome, an anti-αV Fab having a free sulhydryl near the C-terminus was attached to the active end of the PEG chains previously inserted as Mal-PEG-DSPE. Liposome formulations having various antibody:liposome ratios were prepared. In an alternate method of attaching an anti-αV Fab, a Fab having a free sulhydryl near the C-terminus can be conjugated to the Mal-PEG-DSPE and the Fab-PEG-DSPE conjugate inserted into pre-formed liposomes as taught in Example 3 and Example 9. While Example 12 is directed to a scFv that is conjugated to a post MalPEG-DSPE inserted liposome, other sc antibodies exist that do not denature in insertion conditions and may also be inserted into pre-formed, preloaded liposomes at various ligand to liposome ratios.

In certain embodiments the alphaV-targeted liposome of the invention described in the examples set forth below, the alphaV-targeted immunoliposomes were characterized, in vitro and in certain examples, in vivo.

III. Methods of Use

The liposomes can include a therapeutic or diagnostic agent in entrapped form. Entrapped is intended to include encapsulation of an agent in the aqueous core and aqueous spaces of liposomes as well as entrapment of an agent in the lipid bilayer(s) of the liposomes. Agents contemplated for use in the composition of the invention are widely varied, and examples of agents suitable for therapeutic and diagnostic applications are given below.

The targeting ligand included in the liposomes serves to direct the liposomes to a region, tissue, or cell bearing $\alpha v \beta 3$, $\alpha v \beta 5$ integrin, or other αv-subunit containing integrin receptors. Targeting the liposomes to such a region achieves site specific delivery of the entrapped agent. Disease states having a strong $\alpha v \beta 3$, $\alpha v \beta 5$ vascular disorders or osteoporosis ($\alpha v \beta 3$); tumor angiogenesis, tumor metastasis, tumor growth, multiple sclerosis, neurological disorders, asthma, vascular injury or diabetic retinopathy ($\alpha v \beta 3$ or $\alpha v \beta 5$); and, angiogenesis (both $\alpha v \beta 3$ and $\alpha v \beta 5$).

Additionally, $\alpha v \beta 3$ inhibitors or agents which block ligand binding to the receptor have been found to be useful in treating diseases characterized by excessive or inappropriate angiogenesis (i.e. formation of new blood vessels) and inhibiting neoplastic growth and tumor metastasis. Consequently the delivery of an appropriate therapeutic agent to would be expected to enhance this effect.

Moreover, the growth of tumors depends on an adequate blood supply, which in turn is dependent on the growth of new vessels into the tumor; thus, inhibition of angiogenesis can cause tumor regression in animal models (Harrison's Principles of Internal Medicine, 1991, 12th ed.). Therefore, an αv-subunit containing integrin-targeted liposome containing a therapeutic agent, which inhibit angiogenesis can be useful in the treatment of cancer by inhibiting tumor growth (Brooks et al., *Cell,* 79:1157-1164 (1994)). Evidence has also been presented suggesting that angiogenesis is a central factor in the initiation and persistence of arthritic disease and that the vascular integrin $\alpha v \beta 3$ may be a preferred target in inflammatory arthritis. Therefore, $\alpha v \beta 3$ targeted liposomes that deliver an anti-angiogenesis or appropriate therapeutic drug to treat arthritis may represent a novel therapeutic approach to the treatment of arthritic disease, such as rheumatoid arthritis (C. M. Storgard et al., *J. Clin. Invest.,* 103:47-54 (1999)).

Inhibition of the $\alpha v \beta 5$ integrin receptor can also prevent neovascularization. A monoclonal antibody for $\alpha v \beta 5$ has been shown to inhibit VEGF-induced angiogenesis in rabbit cornea and the chick chorioallantoic membrane model (M. C. Friedlander et al., *Science,* 270:1500-1502 (1995)). Thus, anti-alphaV targeted liposomes, which will naturally target $\alpha v \beta 5$, containing an appropriate therapeutic agent would be useful for treating and preventing macular degeneration, diabetic retinopathy, cancer, and metastatic tumor growth.

Inhibition of αβ integrin receptors can also prevent angiogenesis and inflammation by acting as antagonists of alphaV-subunit integrins comprising other β subunits, such as $\alpha v \beta 6$ and $\alpha v \beta 8$ (Melpo Christofidou-Solomidou et al., *American Journal of Pathology,* 151:975-83 (1997); Xiao-Zhu Huang et al., *Journal of Cell Biology,* 133:921-28 (1996)), again suggesting in disease states where angiogenesis or inflammation is to be treated that a $\alpha v \beta 6$ targeted liposome containing an appropriate therapeutic agent would provide a novel therapy.

More generally, the anti-alpha-V subunit antibodies or specified variants thereof can be used to measure or effect in an cell, tissue, organ or animal (including mammals and humans), to diagnose, monitor, modulate, treat, alleviate, help prevent the incidence of, or reduce the symptoms of, at least one condition mediated, affected or modulated by alpha V integrins. Such conditions are selected from, but not limited to, diseases or conditions mediated by cell adhesion and/or angiogenesis. Such diseases or conditions include an immune disorder or disease, a cardiovascular disorder or disease, an infectious, malignant, and/or neurologic disorder or disease, or other known or specified alpha-V integrin subunit related conditions. In particular, the antibodies are useful for the treatment of diseases that involve angiogenesis such as disease of the eye and neoplastic disease, tissue remodeling such as restenosis, and proliferation of certain cells types particularly epithelial and squamous cell carcinomas. Particular indications include use in the treatment of atherosclerosis, restenosis, cancer metastasis, rheumatoid arthritis, diabetic retinopathy and macular degeneration. The neutralizing antibodies of the invention are also useful to prevent or treat unwanted bone resorption or degradation, for example as found in osteoporosis or resulting from PTHrP overexpression by some tumors. The antibodies may also be useful in the treatment of various fibrotic diseases such as idiopathic pulmonary fibrosis, diabetic nephropathy, hepatitis, and cirrhosis.

Thus, in one embodiment, the present invention provides a method for modulating or treating at least one alpha-V subunit related disease, in a cell, tissue, organ, animal, or patient, as known in the art or as described herein, using at least one alpha-V subunit antibody of the present invention. One preferred indication are malignant diseases in a cell, tissue, organ, animal or patient. Malignant diseases include, but are not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, pancreatic carcinoma, renal cell carcinoma, breast cancer, nasopharyngeal carcinoma, malignant histiocytosis, paraneoplastic syndrome/hypercalcemia of malignancy, solid tumors, adenocarcinomas, squamous cell carcinomas, sarcomas, malignant melanoma, particularly metastatic melanoma, hemangioma, metastatic disease, cancer related bone resorption, cancer related bone pain, and the like.

The immunoliposome includes an agent entrapped within the liposome. The agent is entrapped in either or both of the aqueous spaces and/or the lipid bilayers. The agent is an active, typically a therapeutic agent, which includes natural and synthetic compounds having the following therapeutic activities including but not limited to: steroids, immunosuppressants, antihistamines, non-steroidal anti-asthamtics, non-steroidal anti-inflammatory agents, cyclooxygenase-2 inhibitors, cytotoxic agents, gene therapy agents, radiotherapy agents, and agents capable of gene knockdown. Imaging agents may also be used in the targeted liposomes particularly with regard to diagnosis or imaging of patients who have cells and tissues sensitized to alphaV-targeted liposomes.

Examples of these compounds include (a) steroids such as beclomethasone, methylprednisolone, betamethasone, prednisone, dexamethasone, and hydrocortisone; (b) immunosuppressants such as FK-506 type immunosuppressants; (c) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (d) non-steroidal anti-asthmatics such as beta2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (e) non-steroidal antiinflammatory agents (NSAIDs) such as propionic acid derivatives (alminoprofen, benoxaprofen, bucloxic acid, qarprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (f) cyclooxygenase-2 (COX-2) inhibitors such as celecoxib, rofecoxib, and parecoxib; (g) cholesterol lowering agents such as HMG-CoA reductase inhibitors (lovastatin, simvastatin, pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (h) anti-diabetic agents such as insulin, sulfonylureas, biguanides (metformin), α-glucosidase inhibitors (acarbose) and glitazones (troglitazone, pioglitazone, englitazone, MCC-555, BRL49653 and the like); (1) agents that interfere with TNF such as antibodies to TNF (REMICADE®) or soluble TNF receptor (e.g. ENBREL®); (h) anticholinergic agents such as muscarinic antagonists (ipratropium and tiatropium); (i) antimetabolites such as azathioprine and 6-mercaptopurine, and cytotoxic cancer chemotherapeutic agents.

The entrapped therapeutic agent is, in one embodiment, a cytotoxic drug. The drug can be an anthracycline antibiotic, including but not limited to doxorubicin, daunorubicin, epirubicin, and idarubicin, including salts and analogs thereof. The cytotoxic agent can also be a platinum compound, such as cisplatin, carboplatin, ormaplatin, oxaliplatin, zeniplatin, enloplatin, lobaplatin, spiroplatin, ((−)-(R)-2-aminomethylpyrrolidine (1,1-cyclobutane dicarboxylato)platinum), (SP-4-3(R)-1,1-cyclobutane-dicarboxylato(2-)-(2-methyl-1, 4-butanediamine-N,N')platinum), nedaplatin and (bis-acetato-ammine-dichloro-cyclohexylamine-platinum(IV)).

The cytotoxic agent can also be a topoisomerase 1 inhibitor, including but not limited to topotecan, irinotecan, (7-(4-methylpiperazino-methylene)-10,11-ethylenedioxy-20(S)-camptothecin), 7-(2-(N-isopropylamino)ethyl)-(20S)-camptothecin, 9-aminocamptothecin and 9-nitrocamptothecin. The cytotoxic agent can also be a vinca alkaloid such as vincristine, vinblastine, vinleurosine, vinrodisine, vinorelbine, and vindesine. The entrapped therapeutic agent can also be an angiogenesis inhibitor, such as angiostatin, endostatin and TNF.

Nucleic acids are also contemplated for use as the therapeutic agent. DNA and RNA based nucleic acids, including fragments and analogues, can be used for treatment of various conditions, and coding sequences for specific genes of interest can be retrieved from DNA sequence databanks, such as GenBank or EMBL. For example, polynucleotides for treatment of viral, malignant and inflammatory diseases and conditions, such as, cystic fibrosis, adenosine deaminase deficiency and AIDS, have been described. Treatment of cancers by administration of tumor suppressor genes, such as APC, DPC4, NF-1, NF-2, MTS1, RB, p53, WT1, BRCA1, BRCA2 and VHL, are contemplated. Administration of the following nucleic acids for treatment of the indicated conditions are also contemplated: HLA-B7, tumors, colorectal carcinoma, melanoma; IL-2, cancers, especially breast cancer, lung cancer, and tumors; IL-4, cancer; TNF, cancer; IGF-1 antisense, brain tumors; IFN, neuroblastoma; GM-CSF, renal cell carcinoma; MDR-1, cancer, especially advanced cancer, breast and ovarian cancers; and HSV thymidine kinase, brain tumors, head and neck tumors, mesothelioma, ovarian cancer.

The polynucleotide can be an antisense DNA oligonucleotide composed of sequences complementary to its target, usually a messenger RNA (mRNA) or an mRNA precursor. The mRNA contains genetic information in the functional, or sense, orientation and binding of the antisense oligonucleotide inactivates the intended mRNA and prevents its translation into protein. Such antisense molecules are determined based on biochemical experiments showing that proteins are translated from specific RNAs and once the sequence of the RNA is known, an antisense molecule that will bind to it through complementary Watson-Crick base pairs can be designed. Such antisense molecules typically contain between 10-30 base pairs, more preferably between 10-25, and most preferably between 15-20. The antisense oligonucleotide can be modified for improved resistance to nuclease hydrolysis, and such analogues include phosphorothioate, methylphosphonate, phosphodiester and p-ethoxy oligonucleotides (WO 97/07784). The entrapped agent can also be a ribozyme or catalytic RNA.

Typically, treatment of pathologic conditions is effected by administering an effective amount or dosage of an anti-alpha-V subunit antibody immunoliposome composition. In some patients and for some conditions, the anti-alpha V antibody has a therapeutic activity, and in these situations the amount of antibody administered can range, on average, from at least about 0.01 to 500 milligrams of at least one anti-alpha-V subunit antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 μg/mL serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

For other patients and for other diseases, the anti-alpha V antibody serves as a targeting ligand, to direct the liposome and its entrapped therapeutic drug to a specific site in vivo. In these cases, the dosage of immunoliposome is selected according to the desired serum concentration of the entrapped therapeutic drug.

For other patients and for other diseases, the anti-alpha V antibody has a therapeutic effect and the entrapped drug has a therapeutic effect. The dosage of the immunoliposome composition will then be selected according to the desired serum concentration of the drug and/or the antibody, as can be determined from in vitro cytotoxicity tests and/or in vivo dosing studies.

The dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. The dosage can be a one-time or a periodic dosage given at a selected interval of hours, days, or weeks.

Any route of administration is suitable, with intravenous and other parenteral modes being preferred.

In another aspect, the invention contemplates a combined treatment regimen, where the immunoliposome composition described above is administered in combination with a second agent. The second agent can be any therapeutic agent, including other drug compounds as well as biological agents, such as peptides, antibodies, and the like. The second agent can be administered simultaneously with or sequential to administration of the immunoliposomes, by the same or a different route of administration.

IV. Examples

The following examples are illustrative in nature and are in no way intended to be limiting.

Materials

Hydrogenated soy phosphatidylcholine (HSPC) was purchased from Lipoid K. G. (Ludwigshafen, Germany). Cholesterol was received from Croda, Inc. (New York, N.Y.) and N-(carbonyl-methoxypolyethylene glycol 2000)-1,2-distearoyl-sn-glycero-3-phosphatidylethanolamine, sodium salt (mPEG-DSPE) was received from Genzyme (Cambridge, Mass.). Doxorubicin hydrochloride was received from Meiji Seika Kaisha Ltd. (Tokyo, Japan).

Dithioerythritol (DTE), ethylenediaminetetraacetic acid (EDTA), iodoacetamide (IAC), N-ethylmaleimide (NEM), sodium phosphate monobasic, sodium phosphate dibasic, NaCl, and copper (II) chloride dihydrate were purchased from Sigma (St. Louis, Mo.). Maleimide-terminated PEG coupled to DSPE (MalPEG-DSPE) was purchased from Avanti Polar Lipids (Alabaster, Ala.). The desalting columns, HiTrap SP HP ion exchange columns, and the sephacryl 300 size-exclusion columns were purchased from Amersham Biosciences (Piscataway, N.J.).

Example 1

Preparation of Liposomes

1. Liposome Preparation

Liposome-entrapped doxorubicin was prepared using methods previously described (e.g., U.S. Pat. No. 5,013,556). In brief, the lipid components (HSPC, CHOL, mPEG-DSPE at a molar ratio of 56.4:38.3:5.3) were solubilized in ethanol and added to 250 mM ammonium sulfate solution at 60-65° C. The solution was mixed for 1 hour at this elevated temperature to allow for hydration of the lipid components and formation of liposomes. The liposomes were downsized below a mean particle size of 100 nm by extrusion. The process fluid was diafiltered with ammonium sulfate solution to remove the ethanol, followed by sucrose solution to remove the ammonium sulfate in the external liposomal phase. A sample of the post diafiltration process fluid was submitted for phosphorus concentration determination and diluted to a target phosphorus concentration based on the measured value. Doxorubicin was loaded into the liposomes by incubating the liposomal process fluid with doxorubicin drug solution at 60-65° C. for 1 hour. The resulting drug loaded liposomes were cooled and stored at 2-8° C.

Example 2

Preparation of an Anti-Alpha-V Fab Using a Protease

1. Parent Antibody

The isolated parent antibody, CNTO 95, a heterodimer consisting of SEQ ID NO: 1 and SEQ ID NO: 2 as disclosed in U.S. Pat. No. 7,163,681; was desired as the source of Fab' used as a targeting-ligand. CNTO95 is a full-length human antibody of the IgG1k type. The monovalent binding arm, Fab', to be used represents residues 1-234 or the heavy chain (SEQ ID NO: 1) and the entire light chain (SEQ ID NO: 2).

2. Preparation of F(ab')2

Cleavage of CNTO95 with pepsin under conditions to release the Fc portion from the (Fab')2 of the antibody was performed. Starting with CNTO95 purified using Protein A chromatography, the antibody was diafiltered into 0.1M Citrate pH 4.2 to a final concentration of 10 g/L. Pepsin (Sigma Cat no P6887), reconstituted as a stock solution in the same buffer, was added at a final concentration of 100 U Enzyme/mg IgG and allowed to digest for 90 min at 40° C. The digestion was stopped by raising the pH to 6.0 with Tris-base and the material was filter using a 0.22 um cut-off membrane.

CNTO95 F(ab')2 proved to have some affinity for protein A column and therefore, to improve the yield, the pepsin digest was first purified using catiion exchange chromatography Sepharose HP (GE Healthcare, Piscataway N.J., Cat. No. 17-1087-01) prior to it being passed over Protein A conjugated beads (MABSELECT™, GE Healthcare, Piscataway N.J., Cat. No. 17-5199-01) in a flowthrough mode.

The protein was further purified by anion exchange using a Q Sepharose™ XL (GE Healthcare, Cat No. 17-5072-01) in a flowthrough mode. The product is final purified by ultrafiltration using a 30 kDa MW cut-off membrane and finally concentrated to 10 mg/mL with 30 mM $Na_2HPO_4$ pH 6.0.

3. Reduction of F(ab')$_2$

F(ab')$_2$ was diluted with saline to a target protein concentration of 3.5 mg/mL. The pH of the protein solution was adjusted to 6.5 using 1M sodium phosphate monobasic and 1M sodium phosphate dibasic. A 150 mM dithioerythritol (DTE) stock solution was prepared by dissolving the DTE in the correct volume of water. The volume of 150 mM DTE solution to achieve a 13 mM concentration when added to the protein solution was calculated. The protein was placed in a water bath set to 40° C. Sufficient time was allowed for the protein solution to reach 40° C. prior to adding the reducing agent. The correct volume of DTE was added to the protein solution and incubated at 40° C. for 60 minutes while mixing. At the end of the incubation time the protein solution was placed on ice.

DTE was removed by passing the protein solution over a desalting column. The column was prepacked with Sephadex G-25 with a diameter and height of 2.6 and 10 cm respectively. Up to 20 ml of solution could be loaded on the column for separation of protein from reducing agent. For volumes greater than 20 mL, the desalting step was done in batches. The running buffer used was 30 mM sodium phosphate buffer, pH 6.0 that was argon sparged. The low salt concentration of the running buffer allowed for efficient binding of the protein to the ion exchange column in the next step. As a note, ultra pure water (Milli Q system) was used in making all solutions and buffers to minimize any potential contamination of heavy metals that could affect the reoxidation rate. The flow rate over the column was 10 mL/min.

4. Ion Exchange Step

The protein solution was next loaded onto a HiTrap SP HP ion exchange column. The column size was based on loading approximately 10 mg of protein per 1 mL of column packing. The flow rate during the loading step was ½ a column volume per minute. After loading all of the protein, the column was washed with 10 column volumes of 30 mM sodium phosphate buffer, pH 6.0 that was argon sparged in order to remove any residual DTE. Next, the column was washed with 10 column volumes of 30 mM sodium phosphate buffer, pH 6.0 that was air sparged. The protein was eluted from the column with 30 mM sodium phosphate buffer, 60 mM NaCl, pH 6.0 that was air sparged. The purpose for sparging the buffers in air at room temperature was to saturate the buffers with oxygen and make the process reproducible.

The pH of the eluted protein solution was checked and adjusted if necessary to 6.0. The protein concentration of the protein was determined and diluted to a value of 1.02 mg/mL with the same buffer used to elute the protein (30 mM sodium phosphate buffer, 60 mM NaCl, pH 6.0 that was air sparged). The protein solution was placed in a glass container with the appropriate capacity to minimize the headspace in the container and placed in a water bath set to 20° C.

5. Reoxidation Process

A 63.75 μM $CuCl_2$ stock solution was prepared. This low concentration was achieved by first making a 15.94 mM stock solution by dissolving the appropriate amount of $CuCl_2$ in water and performing successive dilutions in water until the final concentration was achieved. 20 μL of the 63.75 μM $CuCl_2$ stock solution was added for every 1 mL of protein solution. After mixing, the protein concentration was 1.00 mg/mL and the $CuCl_2$ concentration was 1.25 μM.

Samples were taken throughout the reoxidation process to monitor the extent of the reoxidation. The samples were run on an HPLC system with a size exclusion column and a running buffer containing SDS. The Fab' peak was resolved from the heavy and light chain peaks allowing for the quantitation of the % Fab' at the time the sample was taken. Based on these results, the time for reoxidation was determined. The time course for the reoxidation process was nearly identical for all batches made with an optimal time for reoxidation of 320 minutes.

6. Maleimide-Terminated PEG Conjugated to DSPE Insertion into Pre-Formed Liposomes MalPEG-DSPE was dissolved in water for injection at a concentration of 10 mg/mL. The volume of MalPEG-DSPE solution to add to the liposomal solution was calculated based on 1) the phosphorus concentration of the post drug loaded liposomes, 2) the assumption that each liposome is comprised of 80,000 phospholipids and 3) 800 MalPEG-DSPE molecules are inserted per liposome. The calculated amount of MalPEG-DSPE solution was then added to the appropriate amount of post drug loaded liposomal solution, prepared as in Example 1, and incubated at 60 to 65° C. for 1 hour followed by cooling in an ice bath. 9% NaCl solution was added to the process fluid at a volume ratio of 1 to 9 to bring the solution up to 0.9% NaCl concentration. Addition of salt was deemed necessary to minimize any potential Fab' denaturation under low salt conditions during the conjugation step. The solution pH was adjusted to 6.0 using either 1M sodium phosphate monobasic or 1M sodium phosphate dibasic. The preparation of the inserted liposomal material was typically completed a couple of hours prior to the conjugation step to minimize any potential inactivation of MalPEG-DSPE over time.

7. Conjugation Step

At the end of reoxidation, the appropriate volume of protein solution was added to the post MalPEG-DSPE inserted liposomes to begin the conjugation process. The amount of protein required was calculated based on 1) the desired Fab to liposome ratio, 2) the assumption that each liposome is comprised of 80000 phospholipid molecules, 3) phosphorus concentration of the post inserted solution and 4) the assumption that 50% of the protein in solution will conjugate as Fab. The last assumption was based on small-scale optimization work. For some of the later batches produced, EDTA solution was added to the liposomal and protein solutions to achieve a 1 mM concentration in the final mixture. This addition minimized any potential reoxidation during the conjugation process. Conjugation was at room temperature for 2 hours followed by overnight storage at 2-8° C.

8. Quenching and Final Column Purification

The conjugated liposomal formulations were quenched at a 1 mM cysteine concentration for 10 minutes prior to loading on the size exclusion column. The column contained sephacryl-300 packing with a diameter/height of 1.6/60 or 2.6/60 cm depending on the volume of solution to load on the column. A large volume (20% of the column volume) could be loaded on the column due to the large size difference between the liposomes and the unconjugated protein. The column removed unconjugated protein, unreacted cysteine and unencapsulated doxorubicin. The running buffer was 10 mM histine in saline, pH 6.5. The liposomal fraction was concentrated to a target drug concentration of 2.0 mg/mL with a centri prep concentrator with a 100K MWCO membrane at 2800 rpm.

The final formulations were submitted for potency, % drug encapsulation, particle size, pH, % Fab insertion and endotoxin. The reoxidation process was evaluated through analysis of both blocked and conjugated samples taken throughout the process. The samples were analyzed by SDS gel electrophoresis and the bands were quantified by densitometry measurements. Tables 1A-1B below summarize the characteristics of two batches of liposomes.

Example 3

In Vitro Plasma Dissolution of Targeting Ligand from Liposomes

The purpose of this study was to evaluate in-vitro plasma stability of alpha-integrin targeted liposomes with prepared by the method of Example 1 using a Fab as targeting ligand at a ratio of 15:1 ligand to liposome, at 37° C.

1. Preparation of I-125 Fab-PEG-DSPE

Fab-PEG-DSPE was mixed with prepared iodobeads for 20 minutes and then placed over 2 desalting columns to separate the I-125 Fab-PEG-DSPE from free I-125. The concentration of the protein was determined by UV absorbance at 280 nm for each of the protein fractions collected. The protein fractions were pooled from each column with the highest protein concentration 2. Preparation of 125-I-Fab' Conjugated STEALTH® Liposomal Doxorubicin Liposomes with entrapped doxorubicin were prepared as set forth in Example 1 and then incubated with sufficient I-125Fab-PEG-DSPE to generate a 15:1 Fab/liposome ratio at 60° C. for 1 hour to allow insertion of the I-125Fab-PEG-DSPE conjugate. At the end of the incubation the solution was cooled and subsequently stored at 2-8° C. Post-insertion material was passed through sepharose-CL-4B column to remove un-inserted Fab-PEG-DSPE. The final formulation was characterized for size, pH, doxorubicin concentration, doxorubicin encapsulation, Fab-PEG-DSPE insertion and Fab-PEG-DSPE concentration. The liposome characteristics are summarized in Table 2A.

TABLE 2A

| Fab:Liposome Ratio | Potency (mg/mL) | Particle Size (nm) 90°/30° | % Drug Encapsulation | % Fab-PEG-DSPE Insertion | Fab-PEG-DSPE Concentration (μg/mL) |
|---|---|---|---|---|---|
| 15:1 | 2.02 | 134/153 | 99 | 97 | 74.05 |

TABLE 1A

Characteristics of targeted liposomes in Batch 1

| Batch 1: Targeting ligand:liposome ratio | Potency (mg/mL) | % drug encapsulation | Particle Size (nm) | % insertion |
|---|---|---|---|---|
| 15:1 | 2.21 | 99 | 85 | 98.7 |
| 40:1 | 2.19 | 99 | 87 | 98.8 |
| 90:1 | 2.09 | 97 | 88 | 99.7 |

TABLE 1B

Characteristics of targeted liposomes in Batch 2

| Batch 2: Targeting ligand:liposome ratio | Potency (mg/mL) | % drug encapsulation | Particle Size (nm) | % insertion |
|---|---|---|---|---|
| 15:1 | 2.15 | 99 | 85 | 98.4 |
| 40:1 | 2.12 | 98 | 87 | 98.5 |
| 90:1 | 2.24 | 98 | 90 | 99.5 |

3. Preparation of Sepharose CL-4B Columns

Two 28×1.2 cm columns containing sepharose CL-4B were prepared, each with a bed volume of 32 mL. The columns were pre-conditioned with 1 mL placebo liposomes and 1 mL rat plasma to block any potential binding sites on the column and therefore minimize any binding of samples to the column. The elution buffer used for all samples was saline containing 0.02% sodium azide. The columns were evaluated to assess whether liposomes could be separated from plasma proteins. Placebo liposomes were combined with rat plasma and loaded on the sepharose CL-4B columns. Eluted fractions were collected from each column and the presence of liposomes or proteins was detected by absorbance at 280 nm. Column profiles showed good separation between liposomes and plasma. The recovery of sample from the column was determined by comparing the activity of the unseparated sample to the total activity of all of the fractions collected for that sample. The recovery was greater than 90% for all samples.

4. In Vitro Fab-PEG-DSPE Dissociation in Human Plasma

Human plasma was mixed with 125-I-labeled, targeted liposomes and incubated at 37° C. over 96 hours. At given time points (0, 1, 4, 8, 24, 48, 72, 96 hours) a sample was removed and loaded onto sepharose CL-4B column. Fractions (1 mL each) were collected from the column and the total radioactivity for each fraction was counted using a gamma counter for 125-I radioactivity.

5. Results

The elution profiles of the 125-I Fab-PEG-DSPE conjugate for all sample time points were similar (not shown), with minor profile differences due to column packing efficiencies. Radioactivity in the liposomal fraction were recovered within a very narrow range within 2-3 fractions and typically within 6-9 mL of total eluent collected. Plasma fractions eluted from the sepharose CL-4B column over at least 12 fractions, due to the wide size range of plasma proteins. Over all time points, the liposomal and plasma fraction were distinguishable from each other. In order to calculate percentage of dissociated Fab-PEG-DSPE, the radioactivity from the liposomal (or plasma) fractions were combined to provide a total amount of Fab-PEG-DSPE. That total was assessed as a ratio of total radioactivity in the sample applied to the Sepharose CL-4B column. FIG. 1 and Table 3 show the percentage of Fab-PEG-DSPE conjugate remaining in the liposomes and the percentage of conjugate dissociated from the liposomes as a function of incubation time.

TABLE 3

Percent of 125-I Fab- PEG-DSPE remaining the liposome after incubation in human plasma at 37° C.

| Time (hr) | % of Fab-PEG-DSPE Conjugate in Liposomal Fraction | % of Fab-PEG-DSPE Conjugate in Plasma Fraction |
| --- | --- | --- |
| 0 | 90 | 10 |
| 1 | 89 | 11 |
| 4 | 89 | 11 |
| 8 | 87 | 13 |
| 24 | 89 | 11 |
| 48 | 88 | 12 |
| 72 | 88 | 12 |
| 96 | 88 | 12 |

The data from this study indicated that αv-targeted liposomes are stable in human plasma over 96 hours incubation at 37° C.

Example 4

In Vitro Binding and Internalization

This study evaluates the ability of integrin-targeted liposomes to achieve ligand mediated specific binding, internalization, and cell cytotoxicity in tumor cells bearing a humanized αVβ3/5 integrin receptor, as compared to liposomes lacking a targeting ligand.

1. Cells and Cell Media

Several human tumor cells bearing human αVβ3/5 integrins were used: (1) A375.S2, human melanoma cell line; (2) MDA-MB-231, Human Breast Carcinoma Cell line; (3) A2780, Human Ovarian Carcinoma Cell line; (4) HT29, Human Colon Carcinoma Cell line; (5) A549, Human Lung Carcinoma Cell line. As CNTO95 does not bind murine αVβ3/5 integrin, a murine melanoma cell line, B16F10, was used as a negative control in the study.

The media for each cell line was as follows:
1. A375.S2 cell, MEM (Minimum Essential Medium, ATCC Cat No. 30-2006) with addition of 10% Fetal Bovine Serum (FBS, ATCC, Cat No. 30-2021).
2. MDA-MB-231 cell, Leibovitz's L-15 Medium, (ATCC Cat No. 30-2008) with addition of 10% FBS.
3. A2780 cell, RPMI Medium 1640 (Gibco, Cat No. 22400-089HT29) with addition of 10% FBS.
4. A549 cell, F-12K Medium (ATCC, Cat No. 30-2004) with addition of 10% FBS.
5. B16-F10 cell, DMEM (Dulbecco's Modified Eagles's Medium, ATCC Cat No. 30-2002), with addition of 10% FBS.

Cell viability was assayed using the CellTiter 96 AQueous One Solution Cell Proliferation Assay from Promega (Cat No. G3581). A Spectra Max 250 plate reader was used, with a reading wavelength of 490 nm. Confocal Microscopy was done using a Nikon, Eelipse, E600. An Eppendorf centrifuge 5804 was used.

2. Liposome Compositions

Liposomes were prepared as described in Example 1, except in two aspects. First, Dextran Alexa Fluor 488 (Cat No. D-22910, from Molecular Probes) was included in the hydration buffer during the passive encapsulation step of liposome formation, and after the sizing step dialysis was used to remove any unencapsulated Alexa. Second, instead of inserting Fab-PEG-lipid into the liposome bilayer, maleimide-PEG-lipid (MalPEG-DSPE) was inserted into the liposome bilayer at approximately 800 MalPeg-DSPE per liposome at 60° C. for 1 Hr. The insertion step was followed by the conjugation of the Fab to the reactive end of the lipopolymer. The appropriate amount of Fab was added to the MalPEG-DSPE inserted liposomes to achieve a 90:1 anti-alphaV-Fab targeting ligands per liposome ratio. These liposomes were used in the binding and internalization studies described below.

Liposomes bearing 15:1, 40:1, 90:1 and 180:1 alpha-integrin Fab targeting ligands per liposome and containing doxorubicin were prepared as described in Example 1 and 2. These targeted-liposomes were used in the cytotoxicity assay using the various cells lines, as described below.

3. Binding and Internalization Studies

A375.S2 cells were harvested by scraping and then resuspended to obtain individualized cells and rejuvenated for 1 hour, at 37° C. About 1 million cells of each tumor type were counted and distributed into individual centrifugation tubes. The tubes were spun to obtain a cell pellet.

For binding only studies, the cells were cooled to 4° C. by immersing the cell tubes in ice for 10 minutes and then treating with the targeted liposome composition containing a fluorescent marker (Dextran Alexa Fluor 488) at 4° C. for 30 minutes, with mild shaking (140 rpm). After the 30 minute incubation period, 1 mL of cold serum free media was added, the mixture was vortexed briefly, and the centrifuged. The cell pellet was resuspended with cold serum free media, shaken vigorously (440 rpm) at 4° C. for 10 minutes, and then centrifuged to recover the cell pellet. The cell pellet was left in about 100 μL of cold media and about 8 μL was taken for observation under a confocal microscope. All steps, except observation under the confocal microscope, were conducted at 4° C.

For binding and internalization, the cells were treated with the targeted liposome formulation at 37° C. for 10 min, with mild shaking (140 rpm). Cells were treated with the liposome formulations containing either a doxorubicin payload or a fluorescent marker (Dextran Alexa Fluor 488). Treatment was terminated by adding 1 mL of washing media (serum free), vortexing briefly, and centrifuging to recover a cell pellet The cells in the pellet were resuspend in washing media, vigorously shaken for 10 minutes at 37° C. and then centrifuged again (440 rpm). The cell pellet was left in 100 μL of media, an aliquot of 8 μL was taken and placed on a glass slide for observation under a confocal microscope.

Binding and internalization of the targeted liposomes to A375.S2 cells was evaluated after various incubation times of the cells and the liposome formulation. Results are shown in FIGS. 2-5.

In FIGS. 2A and 2C, confocal microscopy results show that the targeted liposome formulation containing a fluorescent marker (Dextran Alexa Fluor 488) binds specifically to A375.S2 cells at 4° C. in vitro while the corresponding untargeted liposome formulation containing fluorescent marker does not. FIGS. 2B and 2D show images of the cells in "differential interference contrast" mode (DIC) and provides a reference on cell locations for FIGS. 2A and 2C. All subsequent Figures have a DIC pictures that correspond to the confocal image for reference. Confocal microscopy results shown in FIGS. 3A through 3H that liposomes bearing 90:1 alpha-integrin Fab targeting ligands per liposome as described in Examples 1 and 2 ("targeted liposome formulations") specifically bind to A375.S2 cells and internalize into the same cells in vitro. FIGS. 3A and 3B shown cells that were not treated with drug and, as expected, no evidence of binding or internalization was observed. When the cells were treated with free doxorubicin (i.e., nonliposomal drug) in FIGS. 3C and 3D, drug internalization is evident, however, the diffuse fluorescence pattern suggests the mechanism of drug internalization was nonspecific diffusion of drug across the cell membrane. FIGS. 3E and 3F show cells treated with untargeted liposomes containing doxorubicin. No evidence of binding or internalization of these liposomes was observed. Finally, specific binding and internalization of was observed for the targeted liposome formulation (see FIGS. 3G and 3H) and the fluorescence pattern is marked by regions of high fluorescense intensities on the surface and inside the cytoplasm indicative of liposome internalization under the treatment regime described above.

FIG. 4A through 4J show a timecourse study following internalization of the Dextran Alexa Fluor 488 fluorescent marker and doxorubicin (24 hour timepoint only). As the time post-treatment increases, evidence of internalization and penetration into the cytoplasm becomes more clear. More importantly, this data suggests the presence of the fluorescent marker in the cytoplasm may be due to liposome internalization and not fluorescent marker leakage from liposomes followed by diffusion since the fluorescent marker used in this study cannot diffuse across the cell membrane.

FIGS. 5A through 5H show results from a similar experiment shown in FIG. 3A through 3H. The one change in the experimental conditions was the use of a murine cell line B16.F10 that does not express alpha-V integrins on its cell surface. The purpose of this experiment was to show that liposomes bearing 90:1 alpha-integrin Fab targeting ligands per liposome as described in Examples 1 and 2 only bind to cells expressing alpha-V. The confocal microscopy images demonstrate that this is the case. No binding was observed in this cell line which suggests alpha-V targeted liposomes have a high degree of specificity for alpha-V over-expressing tumor types.

4. Method of Cytotoxicity Assay

Cells were harvested by scraping and then resuspended at 37° C. for 1 hour to obtain individualized cells. About 1 million cells of each tumor type were counted and placed in individual centrifugation tubes. The tubes were centrifuged to obtain a cell pellet. The cells were then incubated with the targeted liposome compositions containing doxorubicin for 10 minutes at 37° C., with mild shaking, 140 rpm. Cells were treated with a quantity of liposomes sufficient to give a doxorubicin concentration of 40 μg/mL. After the 10 minute period, 1 mL of washing media (serum free) was added, the cells were vortexed briefly and then centrifuged to obtain a cell pellet. The pellet was resuspended in serum free washing media, vigorously shaking for 10 minutes at 37° C., 440 rpm. After centrifuging again, 1 mL of media containing 10% fetal bovine serum was added. Cells from each tube were seeded on a plate at a concentration of 2000 cell/well, in triplicate for each point. The plate was incubated for 3 and 6 days and then a cell viability assay for cell growth inhibition was conducted.

The images (FIGS. 6-9) from the binding study show that alpha-V targeted liposomes specifically bind, and are internalized by the αVβ3/5 integrin positive A375.S2 human melanoma cells. Internalization was time dependent and at longer exposure times, cells internalized a greater number of liposomes. Internalization occurs rapidly, with cells exposed to targeted liposomes for 10 minutes achieving internalization of liposomes into the cell cytoplasm. The presence of liposomes in the nucleus of the cells was also observed in the confocal microscopy images.

The alpha-integrin targeted liposomes displayed specific cytotoxicity toward human αVβ3/5 integrin positive cell lines, including A375.S2, MDA-MB-231, and A2780. As expected, the alpha-V targeted liposomes had no binding to the murine cell line used as a negative control, B16.F10 cell.

The data obtained from the cytotoxicity studies was used to determine molar concentration of each doxorubicin-containing liposomes formulation that produced 50% of the maximum possible response ($IC_{50}$). $IC_{50}$ values were determined for doxorubicin in free form, doxorubicin entrapped in liposomes lacking the targeting antibody fragment, and doxorubicin entrapped in liposomes bearing targeting ligands at densities of 40:1 and 90:1 when applied to melanoma tumor cells (A375.S3), breast cancer cells (MDA-MD-231), human ovarian cancer cells (A2780), colon cancer cells (HT29), lung cancer cells (A549), and the non-integrin bearing B16-F10 cells. The values are summarized in Table 4 where the "Increase" corresponds to ratio of $IC_{50}$ value for liposome-entrapped doxorubicin to the $IC_{50}$ value for integrin-targeted liposome-entrapped doxorubicin bearing 90:1 ligand:liposome.

TABLE 4

$IC_{50}$ Values of doxorubicin in various formulations

| Tumor Cell Line | free dox | liposome-entrapped dox | integrin targeted liposome-entrapped dox 40:1 | integrin targeted liposome-entrapped dox 90:1 | Increase |
|---|---|---|---|---|---|
| melanoma AS375.S2 | >200 | 32 | 15 | 7 | 29 |
| breast cancer MDA-MS-231 | >200 | 110 | 45 | 52 | 5 |
| ovarian cancer A2780 | >200 | 9 | 12 | 7 | 29 |
| colon cancer HT29 | >200 | >200 | 180 | >200 | 1.1 |
| Lung cancer A549 | >200 | >200 | >200 | >200 | 1 |

TABLE 4-continued

IC$_{50}$ Values of doxorubicin in various formulations

| Tumor Cell Line | free dox | liposome-entrapped dox | integrin targeted liposome-entrapped dox 40:1 | integrin targeted liposome-entrapped dox 90:1 | Increase |
|---|---|---|---|---|---|
| Murine melanoma B16-F10 | >200 | 33 | na | >200 | 1 |

These data show that certain human tumor derived cell lines are sensitized to the alphaV-targeted liposomes.

Example 5

Pharmacokinetic Profiles of Integrin-Targeted Liposomes in Mice

The objective of this study was to determine the pharmacokinetic profiles of liposomes bearing Fab' targeting ligands, prepared as in Example 1 and 2, for $\alpha_v$ integrin after a single intravenous (IV) bolus administration in female CD-1 mice. Four different formulations with varying Fab' to liposome ratios, i.e., 15, 40, 90, and 180 were tested and compared to the pharmacokinetic profile of a liposomes lacking a targeting ligand.

1. Liposome Compositions

Liposomes lacking an integrin targeting ligand, referred to as "S-DOX", were prepared as described in Example 1.

AlphaV-targeted liposomes, referred to as "Fab' S-DOX", were also prepared as described in Example 2. The four integrin-targeted liposome formulations were:

- 15:1 Fab' to liposome ratio—The doxorubicin concentration was 2.15 mg/mL and encapsulation was 99%. The average diameter of liposomes in the final formulation was 85 nm.
- 40:1 Fab' to liposome ratio—The doxorubicin concentration was 2.12 mg/mL and encapsulation was 98%. The average diameter of liposomes in the final formulation was 87 nm.
- 90:1 Fab' to liposome ratio—The doxorubicin concentration was 2.24 mg/mL and encapsulation was 98%. The average diameter of liposomes in the final formulation was 90 nm.
- 180:1 Fab' to liposome ratio—The doxorubicin concentration was 2.03 mg/mL and encapsulation was 95%. The average diameter of liposomes in the final formulation was 90 nm.

The test formulations are summarized in the Table 5.

TABLE 5

Summary of Liposome Test Formulations

| Group No. | No. of Animals | Dose Route | Formulation | Fab' to liposome ratio | Dose (mg/kg) | Drug Dosing Concentration (mg/mL) |
|---|---|---|---|---|---|---|
| 1 | 18 | IV | S-DOX | 0 | 2 | 0.2 |
| 2 | 18 | IV | Fab'-S-DOX | 15:1 | 2 | 0.2 |
| 3 | 18 | IV | Fab'-S-DOX | 40:1 | 2 | 0.2 |
| 4 | 18 | IV | Fab'-S-DOX | 90:1 | 2 | 0.2 |
| 5 | 18 | IV | Fab'-S-DOX | 180:1 | 2 | 0.2 |

Sterile saline obtained from a commercial source (Abbott Labs, Lot 31-115-JT, expiration date January 2007) was used for drug dilution prior to administration.

2. Study Design

Sixty female CD-1 mice (Charles River Laboratories, Hollister, Calif.), approximately 20 to 26 g body weight were used for the study. Animals were maintained in isolator cages on a 12-hour light-and-dark cycle. Food and water were available ad libitum.

All animals were administered a single bolus injection of one of the test formulations via a lateral tail vein. Dose volumes were calculated for each individual animal by body weight, ranging from 0.21 to 0.26 mL. Mice were warmed prior to injection in a rodent hotbox. Doxorubicin dose for all treatment groups was 2 mg/kg.

Clinical observations and body weights were recorded prior to dosing. Animals were observed daily thereafter for morbidity and mortality.

Blood samples (about 0.6 mL each) were collected from three mice per time point (5 min, 4, 8, 24, 48, and 96 hr). Blood samples were collected either via cardiac puncture or the hepatic portal vein under inhaled anesthesia (oxygen/Isoflurane) into heparin-coated syringes and immediately transferred into a polypropylene eppendorf tube. The blood sample collection procedure was terminal. Blood samples were then stored on wet ice until centrifugation at 10,000 RPM for 5 minutes at ~4° C. Plasma samples were collected and stored at −20° C. Total doxorubicin concentrations were analyzed by LC/MS.

Since each plasma sample was obtained from an individual animal, the pharmacokinetic (PK) parameters were calculated using the mean plasma doxorubicin concentrations and therefore no standard deviations are present for the PK parameters. All PK parameters were calculated using WIN-NONLIN version 4.1 (Pharsight Corp., Mountain View, Calif.).

3. Results

Figure 10:
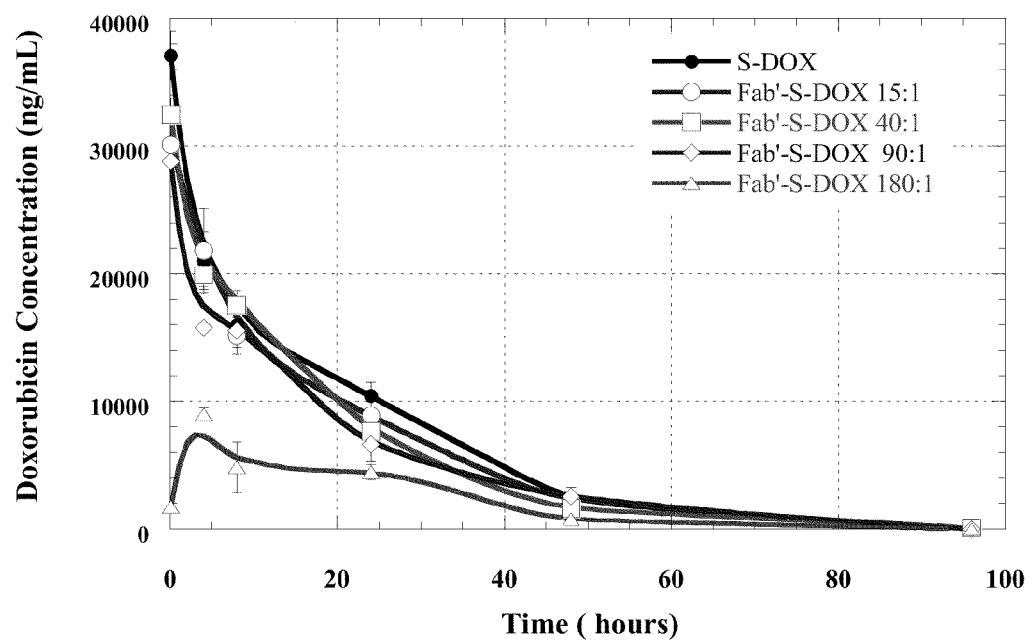
FIG. 10 is a graph showing the doxorubicin concentration, in ng/mL, as a function of time, in hours, after a single bolus intravenous injection into mice of liposomes containing entrapped doxorubicin and lacking a targeting ligand ("S-DOX", closed circles) or bearing alpha-integrin Fab targeting ligands at Fab: liposome ratios of 15:1 (open circles), 40:1 (open squares), 90:1 (open diamonds), and 180:1 (open triangles)

Pharmacokinetic profiles of all test formulations are shown in FIG. 10 and are summarized in Table 6.

TABLE 6

Plasma PK Parameters of Doxorubicin Following a Single IV Administration of Fab'-S-DOX Formulations

| Formulation | $C_{max}$ (±SE, ng/mL) | $T_{max}$ | $AUC_{last}$ (ng-h/mL) | $T_{1/2}$ (h) | Cl (mL/h) |
|---|---|---|---|---|---|
| S-DOX | 37,133 ± 1,868 | 5 min | 554,035 | 13.6 | 0.0838 |
| Fab'-S-DOX 15:1 | 30,133 ± 1,009 | 5 min | 562,945 | 14.4 | 0.0883 |
| Fab'-S-DOX 40:1 | 32,467 ± 1,225 | 5 min | 536,216 | 11.6 | 0.0928 |
| Fab'-S-DOX 90:1 | 28,833 ± 448 | 5 min | 440,048 | 15.5 | 0.1005 |
| Fab'-S-DOX 180:1 | 8,993 ± 499 | 4 h | 186,095 | 14.3 | 0.2480 |

Results showed that plasma concentration peaked by the first sampling time point (within 5 min) for all Fab'-S-DOX formulations except for the one with 180 Fab' per liposome, which peaked at the 4 h time point. $C_{max}$ was 37133, 30133, 32467, 28833, and 8993 ng/mL for Fab'-S-DOX formulations containing Fab'/liposome ratios of 0, 15, 40, 90, and 180, respectively. The $AUC_{last}$ values were similar for those with Fab'/liposome ratios of 0, 15, and 40 (536216 to 562945 ng-h/mL), slightly lower for the ratio of 90 (440048 ng-h/mL), and considerably lower for the ratio of 180 (186095 ng-h/mL). Plasma half-lives were also similar for 4/5 test formulations, ranging between 13.6 to 15.5 h, and the formulation with the Fab'/liposome ratio of 40 had a $t_{1/2}$ of 11.6 h. Drug clearance was also the greatest for the 180 Fab' formulation (0.2480 mL/h) followed by the 0 to 90 Fab' formulations (0.0838 to 0.1005 mL/h).

In this mouse study, similar plasma PK profiles/parameters were observed for the Fab'-S-DOX formulation with Fab'/liposome ratio of 15 or 40 when compared to the non-targeted S-DOX. Fab'-S-DOX formulation with Fab'/liposome ratio of 90 had slightly lower $C_{max}$ and AUC value. Formulation with 180 Fab'/liposome ratio had the lowest (about 70% lower) $C_{max}$ and AUC.

Example 6

Pharmacokinetic Profiles of Integrin-Targeted Liposomes in Rats

The objective of this study was to compare the plasma pharmacokinetic (PK) profile of various Fab' STEALTH® liposomal doxorubicin formulations (Fab'-S-DOX) using surface-conjugated Fab' as a targeting ligand for $\alpha_v$ integrin in rats. The Fab' to liposome ratio in the liposomes were 15:1, 30:1, 60:1, and 90:1.

1. Liposome Compositions

Liposomes lacking an integrin targeting ligand, referred to as "S-DOX", were prepared as described in Example 1.

Integrin-targeted liposomes, referred to as "Fab' S-DOX", were also prepared as described in Example 1 and 2. The four integrin-targeted liposome formulations were:

15:1 Fab' to liposome ratio: the doxorubicin concentration was 2.23 mg/mL and encapsulation was 99%. The average diameter of liposomes in the final formulation was 84 nm.

30:1 Fab' to liposome ratio: the doxorubicin concentration was 2.26 mg/mL and encapsulation was 99%. The average diameter of liposomes in the final formulation was 86 nm.

60:1 Fab' to liposome ratio: the doxorubicin concentration was 2.28 mg/mL and encapsulation was 98%. The average diameter of liposomes in the final formulation was 88 nm.

90:1 Fab' to liposome ratio: the doxorubicin concentration was 2.22 mg/mL and encapsulation was 97%. The average diameter of liposomes in the final formulation was 89 nm.

The test formulations are summarized in the Table 7.

TABLE 7

Summary of Liposome Test Formulations

| Group No. | No. of Rat | Dose Route | Formulation | Fab' to liposome ratio | Dose (mg/kg) | Drug Dosing Concentration (mg/mL) |
|---|---|---|---|---|---|---|
| 1 | 4 | IV | S-DOX | 0 | 1 | 0.4 |
| 2 | 4 | IV | Fab'-S-DOX | 15:1 | 1 | 0.4 |
| 3 | 4 | IV | Fab'-S-DOX | 30:1 | 1 | 0.4 |
| 4 | 4 | IV | Fab'-S-DOX | 60:1 | 1 | 0.4 |
| 5 | 4 | IV | Fab'-S-DOX | 90:1 | 1 | 0.4 |

Sterile saline obtained from a commercial source (Abbott Labs, Lot C665851, expiration date May 2007) was used for drug dilution prior to administration.

2. Study Design

Twenty male CD rats (Charles River Laboratories, Indianapolis, Ind.) were used for the study. The average body weight was 273 g at dosing. Animals were maintained in cages on a 12-hour light-and-dark cycle. Food and water were available ad libitum.

All animals were administered a single bolus intravenous (IV) injection of the test formulation via a lateral tail vein. Dose volumes were calculated for each individual animal by body weight, which ranged from 0.65 to 0.72 mL. Rats were warmed prior to injection in a rodent hotbox. The doxorubicin dose for all treatment groups was standardized to 1 mg/kg. Clinical, observations and body weights were recorded prior to dosing. Animals were observed daily thereafter for morbidity and mortality.

Blood samples (~0.6 mL each) were collected from four rats per time point (2-5 min, 4, 8, 24, 48, and 72 hours). Blood samples were collected under inhaled anesthesia (oxygen/Isoflurane) via the tail vein or orbital sinus into heparin-coated syringes and immediately transferred into a 1 mL polypropylene collection tube. Blood samples were then stored on wet ice until centrifugation at approximately 10,000 RPM for 5 minutes at ~4° C. Plasma samples were collected and stored at −20° C. and total doxorubicin concentration was analyzed by LC/MS.

All PK parameters were calculated using WINNONLIN® version 4.1 (Pharsight Corp., Mountain View, Calif.) and a non-compartment model. Comparison of PK parameters, i.e., $AUC_{last}$, $t_{1/2}$, and observed clearance among test formulations was performed by one-way ANOVA® Tukey analysis.

3. Results

Figure 11:
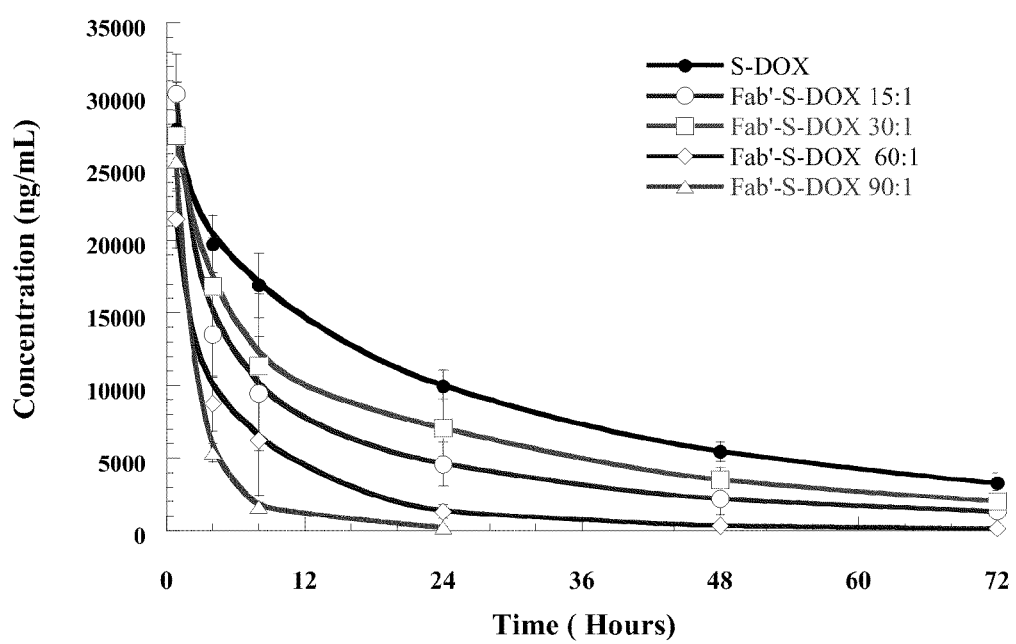
FIG. 11 is a graph showing the doxorubicin concentration, in ng/mL, as a function of time, in hours, after a single bolus intravenous injection into rats of liposomes containing entrapped doxorubicin and lacking a targeting ligand ("S-DOX", closed circles) or bearing alpha-integrin Fab targeting ligands at Fab:liposome ratios of 15:1 (open circles), 30:1 (open squares), 60:1 (open diamonds), and 90:1 (open triangles)

Pharmacokinetic profiles of all test formulations are shown in FIG. 11 and the PK parameters are summarized in Table 8.

TABLE 8

Plasma PK Parameters of Doxorubicin Following a Single IV Administration of Fab'-S-DOX Formulations (Mean ± SD)

| Formulation | Conc. at 5 min (ng/mL) | $AUC_{last}$ (μg-h/mL) | $T_{1/2}$ (h) | Cl (mL/h) |
|---|---|---|---|---|
| S-DOX | 27,650 ± 3,240 | 673 ± 76.6 | 28.3 ± 1.3 | 0.3426 ± 0.04 |
| Fab'-S-DOX 15:1 | 30,075 ± 2,791 | 370 ± 114 | 24.4 ± 3.8 | 0.6964 ± 0.20 |
| Fab'-S-DOX 30:1 | 27,225 ± 3,646 | 486 ± 129 | 26.1 ± 3.0 | 0.5119 ± 0.13 |
| Fab'-S-DOX 60:1 | 21,450 ± 1,984 | 176 ± 51.5 | 12.7 ± 3.0 | 1.6359 ± 0.51 |
| Fab'-S-DOX 90:1 | 25,425 ± 3,538 | 91.6 ± 8.38 | 4.58 ± 0.45 | 2.9527 ± 0.29 |

Results showed plasma concentration peaked at the first sampling time point (within 5 min) for all targeted and non-targeted S-DOX formulations. $C_{max}$ was also similar for 4/5 formulations, which ranged from 25,425 to 30,075 ng/mL but slightly lower for the Fab'-S-DOX 60:1 (21,450 ng/mL). At the 24-h time point, the plasma concentration was the greatest for S-DOX (9,953 ng/mL) followed by Fab'-S-DOX 30:1 (7,063 ng/mL), Fab'-S-DOX 15:1 (4,600 ng/mL), Fab'-S-DOX 60:1 (1,317 ng/mL) and then Fab'-S-DOX 90:1 (222 ng/mL). Similar trend continued for up to 72 h, and drug concentration was un-detectable for Fab'-S-DOX 90:1 starting at the 48 h time point. The $AUC_{last}$ value was also the greatest for S-DOX (673 µg-h/mL) followed by Fab'-S-DOX 30:1 (486 µg-h/mL), Fab'-S-DOX 15:1 (370 µg-h/mL), Fab'-S-DOX 60:1 (134 µg-h/mL) and then Fab'-S-DOX 90:1 (91.6 µg-h/mL). The corresponding $t_{1/2}$ was 28.3, 26.1, 24.4, 12.7, and 4.58 h, and the corresponding clearance was 0.3426, 0.6964, 0.5119, 1.6359, and 2.9527 mL/h.

PK profiles of Fab'-S-DOX formulation vs. S-DOX was performed using the one-way ANOVA® Tukey analysis. For $AUC_{last}$, S-DOX was not different from Fab'-S-DOX 30:1 but was significantly greater than Fab'-S-DOX 15:1 ($p<0.01$), Fab'-S-DOX 60:1 ($p<0.001$), and Fab'-S-DOX 90:1 ($p<0.001$). For $t_{1/2}$, there was no difference between S-DOX and Fab'-S-DOX 15:1 or Fab'-S-DOX 30:1 but $t_{1/2}$ was significantly longer for S-DOX than Fab'-S-DOX 60:1 ($p<0.001$) and Fab'-S-DOX 90:1 ($p<0.001$). Similarly, the clearance was also significantly greater for the Fab'-S-DOX 60:1 and Fab'-S-DOX 90:1 vs. S-DOX ($p<0.001$).

In this rat PK study, it was demonstrated that Fab'-S-DOX formulation with Fab' to liposome ratio of 30:1 had a PK profile similar to the non-targeted liposomal doxorubicin formulation. Fab'-S-DOX formulation with Fab' to liposome ratio of 15 was also similar to that of the liposome formulation having a ratio of 30:1 targeting ligands/liposome. Formulations with Fab' to liposome ratio of 60 or 90 had significantly lower AUC, shorter half-life and greater clearance when compared to the non-targeted formulation.

Example 7

Antitumor Activity of αV-Integrin-Targeted Liposomes in Human Mammary Carcinoma Xenografts The purpose of this study was to evaluate the antitumor activity of $\alpha_V$-integrin targeted Fab' conjugated liposomal doxorubicin (Fab'-S-DOX) on MDA-MB-231 human mammary carcinoma xenografts. Three formulations of Fab'-S-DOX with Fab' to liposome ratio of 15, 40, and 90 were used in the study.

1. Liposome Compositions

Liposomes lacking an integrin targeting ligand, referred to as "S-DOX", were prepared as described in Example 1.

AlphaV-targeted liposomes, referred to as "Fab' S-DOX", were also prepared as described in Example 1 and 2. The three integrin-targeted liposome formulations were:
- 15:1 Fab' to liposome ratio. The doxorubicin concentration was 2.15 mg/mL and encapsulation was 99%. The average diameter of liposomes in the final formulation was 85 nm.
- 40:1 Fab' to liposome ratio. The doxorubicin concentration was 2.12 mg/mL and encapsulation was 98%. The average diameter of liposomes in the final formulation was 87 nm.
- 90:1 Fab' to liposome ratio. The doxorubicin concentration was 2.24 mg/mL and encapsulation was 98%. The average diameter of liposomes in the final formulation was 90 nm.

2. Xenograft Preparation

Female athymic nu/nu homozygous mice (Harlan Laboratories, Indianapolis, Ind.), approximately 5-6 weeks old, were used for the study. The mean body weights were approximately 22 grams. Animals were maintained in isolator cages on a 12-hour light-and-dark cycle. Food and water were available ad libitum.

MDA-MB-231 human mammary carcinoma cells were grown and maintained in culture using Leibovits media with 10% fetal bovine serum. The cells were kept at 37° C. in a humidified incubator. Log-phase cells were trypsinized and harvested from culture flasks and centrifuged at 900 rpm for 10 minutes. The supernatant was discarded and cell pellet re-suspended in Hank's Balanced Salt Solution (HBSS) at $10 \times 10^7$ cells/mL (NB 7301 page 112). The cell suspension was then injected subcutaneously in 100 µL to yield an inoculum of $10 \times 10^6$ cells. The mean tumor size at time of treatment initiation were approximately 150 mm³.

3. Study Design

Treatment groups are summarized in Table 9. Ten animals were assigned to each treatment group. All formulations were administered intravenously (IV) into the lateral tail veins of mice restrained in a heated (40° C.) brass. Immediately prior to each injection, mice were kept warm in a well-ventilated acrylic box with a heating light bulb (ALZA SOP 8-650). Doxorubicin dose was either 1 or 4 mg/kg given once weekly for 4 weeks.

TABLE 9

Study Design for Evaluation of Antitumor Activity of ☐ᵥ Targeted STEALTH ® Liposomal Doxorubicin in MDA-MB-231 Human Mammary Carcinoma Xenografts

| Treatment Groups | Fab'/Liposome ratio | Dose (mg/kg) | Route of Inj. | Dosing Days | No. of Mice |
|---|---|---|---|---|---|
| 1. Untreated Control | N/A | N/A | — | — | 10 |
| 2. S-DOX | 0 | 1 | IV | Day 0, 7, 14, 21 | 10 |
| 3. Fab'-S-DOX | 15:1 | 1 | IV | Day 0, 7, 14, 21 | 10 |
| 4. Fab'-S-DOX | 40:1 | 1 | IV | Day 0, 7, 14, 21 | 10 |
| 5. Fab'-S-DOX | 90:1 | 1 | IV | Day 0, 7, 14, 21 | 10 |
| 6. S-DOX | 0 | 4 | IV | Day 0, 7, 14, 21 | 10 |
| 7. Fab'-S-DOX | 15:1 | 4 | IV | Day 0, 7, 14, 21 | 10 |
| 8. Fab'-S-DOX | 40:1 | 4 | IV | Day 0, 7, 14, 21 | 10 |
| 9. Fab'-S-DOX | 90:1 | 4 | IV | Day 0, 7, 14, 21 | 10 |

Tumors were measured in three dimensions up to 3 times weekly until the average tumor volume for a treatment group reached 1000 mm³ or up to 60 days. Tumor volume was calculated according to the formula:

$$V = \tfrac{1}{2} \times D_1 \times D_2 \times D_3$$

where $D_{1-3}$ are perpendicular diameters measured in millimeters (mm).

Animal body weights were measured three times a week to assess drug toxicity. Clinical observations included behavior or activity within the cage, and signs of pain or distress. All abnormal clinical observations were recorded either in the comment section of the data sheets or the event log. At the end of study period, all animals were provided euthanasia by inhalation of 100% carbon dioxide according to the AVMA Panel on Euthanasia (1993).

Statistical analysis of tumor growth between the various treatment groups was performed by one-way analysis of variance supplemented with a Tukey's multiple comparison post-test (Days 7 to 60) and by Kaplan-Meier Log Rank test (endpoint: time to reach 1000 mm³). Both test were done using GraphPad Prism® 4 software.

4. Results

Figure 12A:
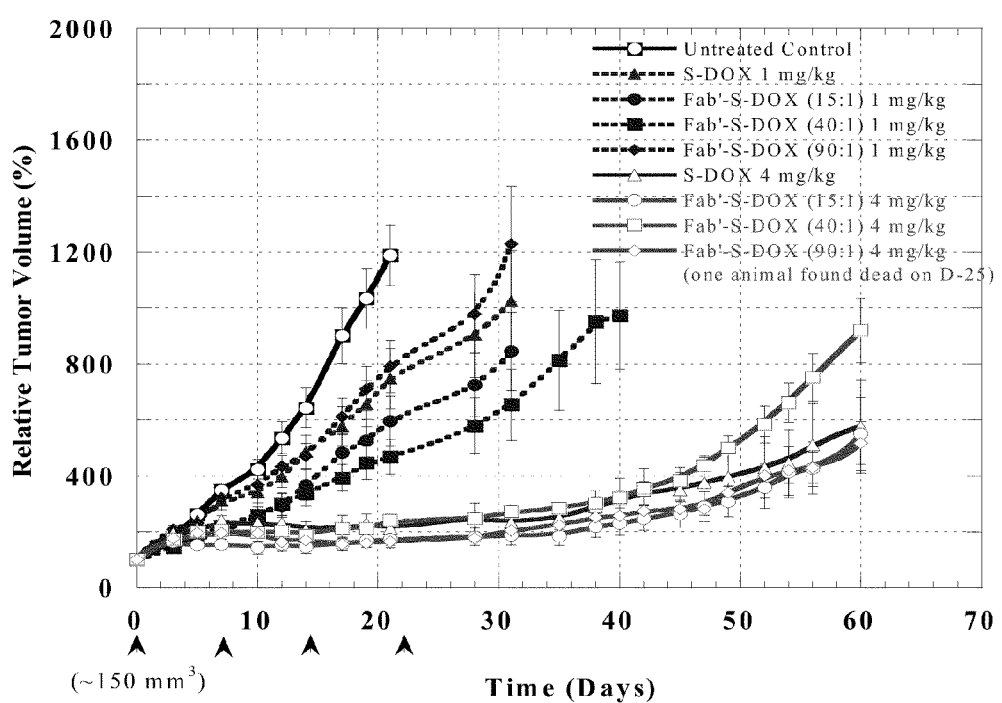
FIGS. 12A-12B are graphs showing the relative tumor volume, in percent (FIG. 12A) and relative body weight, in percent (FIG. 12B), as a function of time, in days, for animals bearing a mammary carcinoma xenograft and left untreated (open squares) or treated with liposomes containing entrapped doxorubicin at doses of 1 mg/kg and 4 mg/kg, the liposomes lacking a targeting ligand ("S-DOX", closed and open triangles) or bearing alpha-integrin Fab targeting ligands at Fab:liposome ratios of 15:1 (closed and open circles), 40:1 (closed and open squares), 90:1 (closed and open diamonds)
Figure 12B:
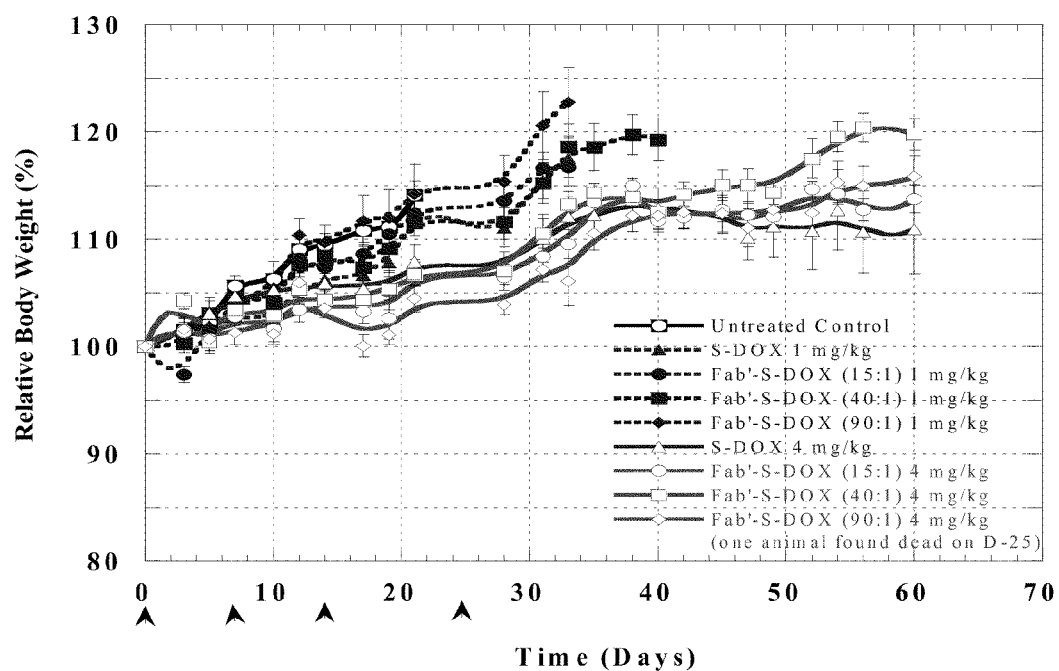
Figure 12C:
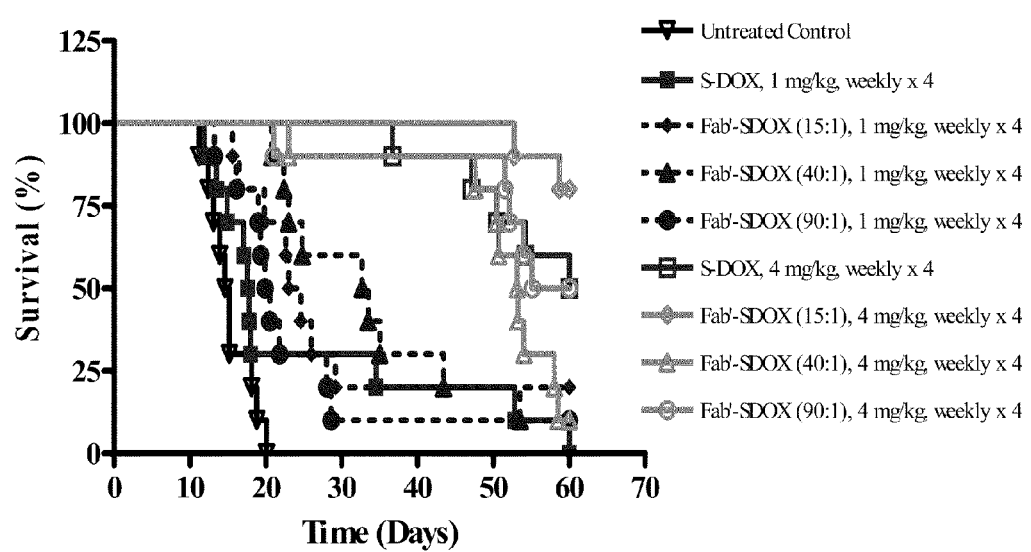
FIG. 12C shows the survival of test animals bearing a mammary carcinoma xenograft as a function of time, in days, the animals left untreated (inverted triangles) or treated with liposomes containing entrapped doxorubicin at doses of 1 mg/kg and 4 mg/kg, the liposomes lacking a targeting ligand ("S-DOX", closed and open squares) or bearing alpha-integrin Fab targeting ligands at Fab:liposome ratios of 15:1 (closed and open diamonds), 40:1 (closed and open triangles), or 90:1 (closed and open circles)

This study evaluated the antitumor activity of $\alpha_v$-targeted liposomal doxorubicin administered IV once weekly for four weeks on MDA-MB-231 human mammary carcinoma xenografts. Tumor growth curves and changes in body weights as a function of time are presented in FIGS. 12A-12B. The tumor growth and body weight are reported as a percent change relative to the initial tumor size and weight for each animal. FIG. 12C shows the survival data for the animals in each treatment group.

The average time for tumor growth to 1000 mm³ volume was 15.2±0.9 days for untreated controls. Tumor in animals treated with S-DOX at 1 and 4 mg/kg reached 1000 mm³ in 25.8±5.5 and 54.8±2.5 days, respectively. Days to 1000 mm³ endpoint for Fab'-S-DOX (15:1, 40:1 and 90:1) treatment group were 29.7±5.2, 34.9±4.3, and 24.6±4.2 days at 1 mg/kg, and 59.1±0.7, 50.8±3.3, and 53.4±3.8 days at 4 mg/kg, respectively. For tumors that had not reached the study endpoint by Day 60, 60-days was used in the data analysis.

No animal body weight loss was observed in all treatment groups. One animal in Fab'-S-DOX (90:1) treatment group at 4 mg/kg was found dead on Day 25:

One way analysis of variance (Days 7 to 60) supplemented with Tukey's post test indicated that all groups treated with 1 mg/kg doxorubicin were similar to untreated control, and those treated with 4 mg/kg formulations had significantly greater antitumor activity than untreated control. The Kaplan-Meier Log Rank Test (endpoint: time to 1000 mm³) indicated a significant antitumor activity for all doxorubicin treatment groups except for S-DOX at 1 mg/kg. However, at each drug dose level, there was no difference between the targeted and non-targeted formulation or between targeted formulations containing different ligand density.

In this study using the MDA-MB-231 human mammary carcinoma xenograft model, similar antitumor activity was observed for S-DOX and Fab'-S-DOX (15:1, 40:1 and 90:1) formulations at the same dose level (1 or 4 mg/kg).

Example 8

Antitumor Activity of AV-Integrin-Targeted Liposomes

This study investigated the ability of integrin-targeted immunoliposomes containing entrapped doxorubicin to inhibit growth of A375S.2 human melanoma tumors in rats.

1. Liposome Compositions

Liposomes lacking an integrin targeting ligand, referred to as "SLD", were prepared as described in Example 1.

Integrin-targeted liposomes, referred to as "ITL", were also prepared as described in Example 1 and 2. Integrin-targeted immunoliposome formulations having 15:1 and 30:1 Fab' to liposome ratios were prepared. The 15:1 formulation had a doxorubicin concentration of 2.23 mg/mL, and the 30:1 formulation had a doxorubicin concentration of 2.26 mg/mL.

2. Xenograft Preparation

Female nude rats approximately 6-8 weeks of age were obtained (Harlan Laboratories, Indianapolis, Ind.). The rats were group-housed (2/cage) in filter-topped plastic cages and supplied with autoclaved food and water. Each animal was tail tattooed with a number or ear tagged prior to the start of the study.

A375S.2 human melanoma tumor cells, free of bacteria and mycoplasma, were cultured in DMEM containing Glutamax, 10% FBS, and 1% non-essential amino acids (complete medium). On the day of the study initiation, cells were trypsinized to generate a single cell suspension, then spun down and resuspended in serum-free DMEM. The final concentration of the cell suspension was $2.5 \times 10^7$ cells/mL.

On day 0, 90 female nude rats were treated with one chewable antibiotic tablet containing 10 mg Trimethoprim and 60 mg sulfamethoxazole (SCID's MD sterile bacon-flavored, Bio-Serv) per cage, once daily. Antibiotic treatment began three to four days before irradiation (Day −5) and continued for two weeks. One day before tumor implantation (Day −1), the animals received 2 rads of whole body irradiation per 1 gram body weight. On Day 0, rats were implanted with 0.2 mL of A375S.2 cell suspension as described above.

Rats were monitored twice a week for appearance of a palpable tumor. When 70 rats had tumors that measured approximately 50-250 mm³ (Day 8), they were stratified into seven groups with 10 animals each, for treatment as set forth in Table 10. Day 8 was the start of treatment. Rats were weighted on the day of drug dosing, and were injected iv at weekly intervals for four total doses with 2 or 0.5 mg/kg of test liposome formulation or were given a saline control.

Tumor growth was measured twice a week with calipers in two dimensions (length and width) in millimeters (mm). Tumor volume (mm³) was calculated based on the formula (length×width×width)/2.

TABLE 10

| Treatment Groups | | | |
|---|---|---|---|
| Group | Treatment | Dose (mg/kg) | Doxorubicin Concentration (mg/mL) |
| 1 | PBS | 1 mL/100 g body weight | 0 |
| 2 | SLD | 2 | 0.2 |
| 3 | ITL 15:1 | 2 | 0.2 |
| 4 | ITL 30:1 | 2 | 0.2 |
| 5 | SLD | 0.5 | 0.05 |
| 6 | ITL 15:1 | 0.5 | 0.05 |
| 7 | ITL 30:1 | 0.5 | 0.05 |

Tumor weight data was analyzed via standard linear model and analysis of variance (ANOVA®). P-values less than 0.05 for all tests and comparisons were deemed significant unless otherwise indicated. A logarithmic scale was used since underlying assumptions of equal variance and normal distribution shape were better satisfied. The zero and 0.5 values, for mice that measured little to no tumor, were replaced with small spline-interpolated value that facilitated statistical analysis in the logarighmic scale without corruption of the data structure.

For the tumor volume, a repeated measures model was fit to the data assuming a first order autocorrelation covariance structure. Natural splines were used to model the curvature of trends in the time profiles. Pairwise correlations amongst the groups were made at each of the timepoints. Calculations were performed using the R software environment.

3. Results

Figure 13A:
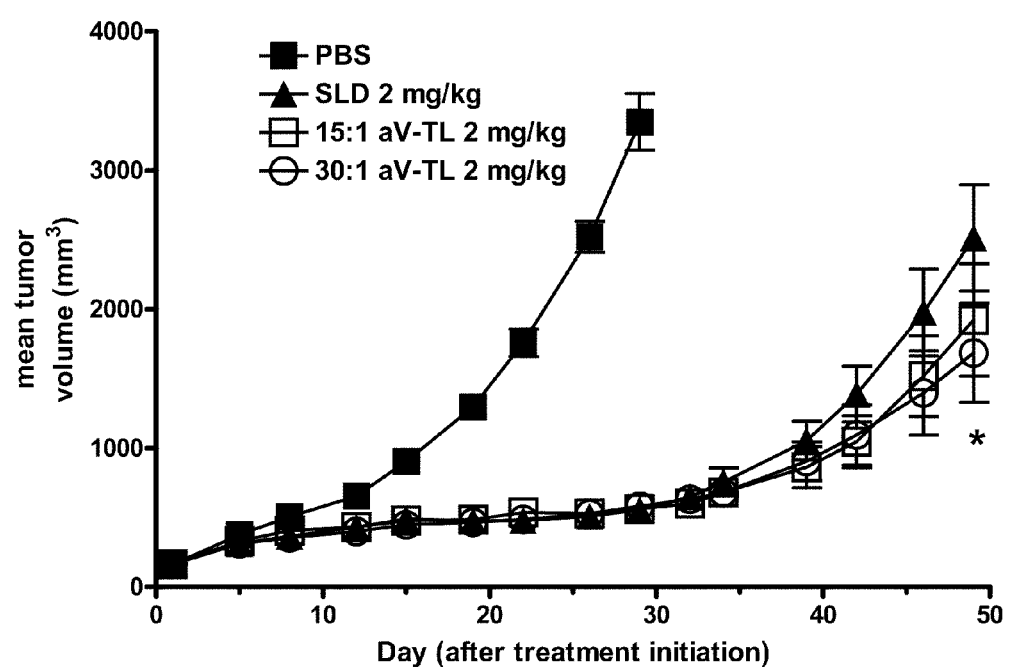
FIGS. 13A-13B are graphs showing the mean tumor volume, in mm³, in rats bearing a human melanoma xenograft, as a function of time, in days, after initiation of treatment with saline, or with doxorubicin a doses of 2 mg/kg (FIG. 13A) or 0.5 mg/kg (FIG. 13B), the doxorubicin entrapped in liposomes lacking a targeting ligand ("SLD") or bearing alpha-integrin Fab targeting ligands at Fab:liposome ratios of 15:1 or 30:1.
Figure 13B:
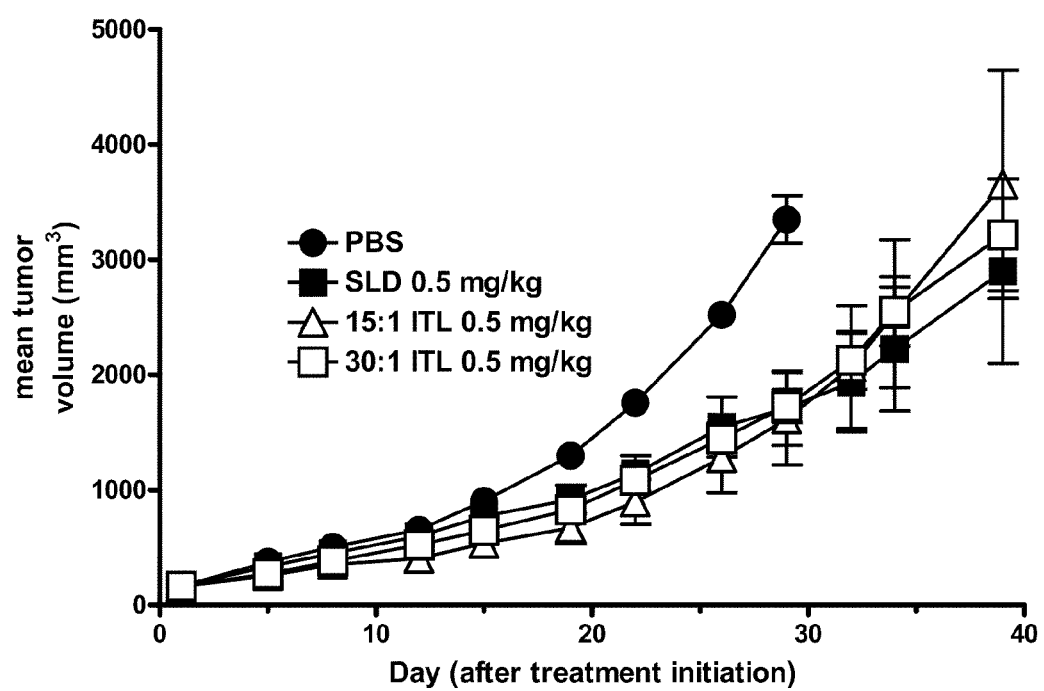
Figure 14A:
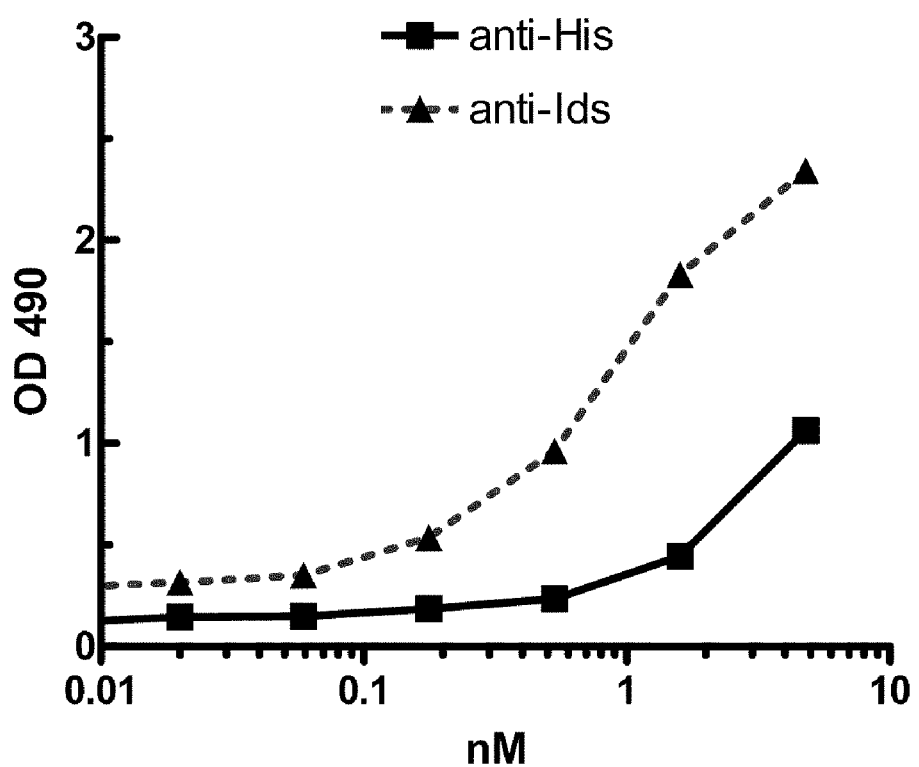
FIG. 14A-14B are graphs showing the binding of CNTO95 derived scFV to alphaVbeta3 (A) or alphaVbeta5 (B) coated plates and detected by binding of either an anti-idiotype antibody (anti-ids) or and antibody to the hexahistidine tail.
Figure 14B:
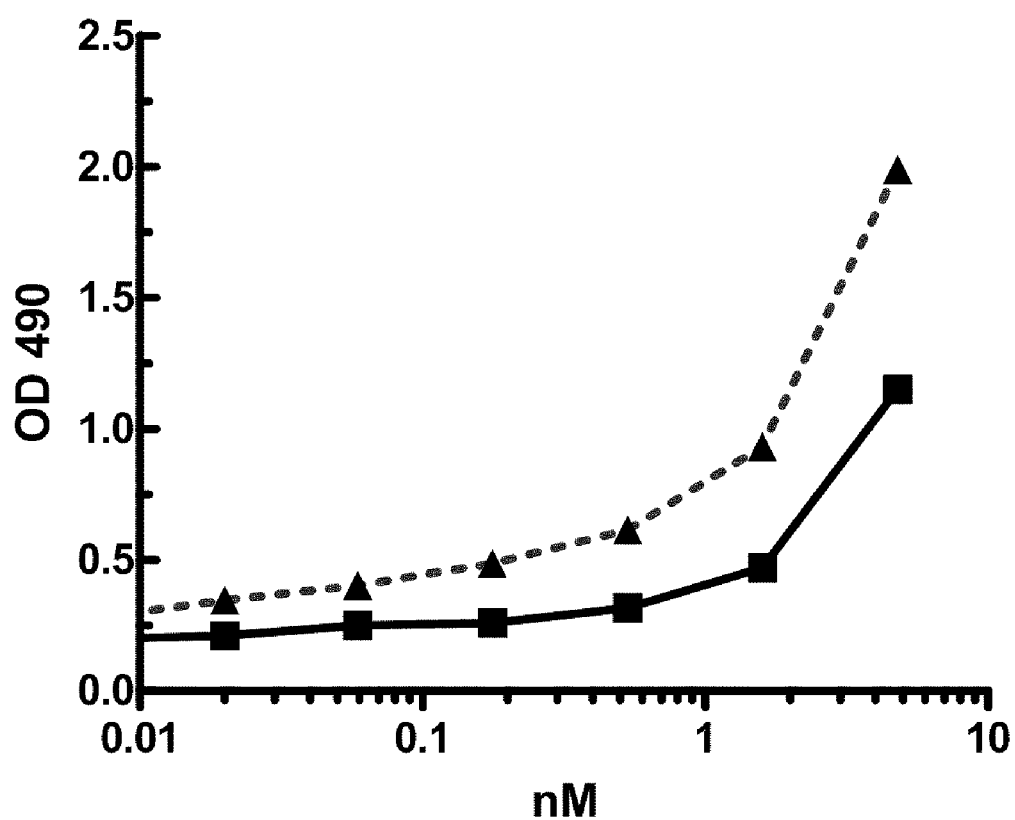

The immunoliposome formulations having 15:1 and 30:1 anti-integrin Fab' antibodies per liposomes were administered once a week for four doses, beginning when the tumors were approximately 165 mm$^3$. Tumor growth curves are shown in FIGS. 13A-13B, for rats treated with 2 mg/kg and 0.5 mg/kg doxorubicin, respectively. The negative control group, PBS treated animals, shows complete tumor take and steady tumor growth, with the group reaching maximal tumor volume in 29 days. All rats treated with doxorubicin entrapped in liposomes lacking a targeting ligand ("SLD") or bearing a targeting ligand ("ITL") showed significantly delayed tumor growth. The 0.5 mg/kg groups reached maximal tumor volume on Day 39 and the 2 mg/kg groups reached maximal tumor volume on Day 49.

The immunoliposomes bearing 15:1 Fab' fragments per liposome showed a trend of tumor growth delay when compared to liposomes lacking a targeting ligand. Accordingly, in a preferred embodiment, immunoliposomes bearing fewer than about 25 targeting ligand per liposome, preferably fewer than 20, and still more preferably about 15 or fewer targeting ligands per liposome, is contemplated.

Example 9

Generation of a Host Cell Line Producing Anti-AlphaV Fab

The CNTO95 heavy chain signal peptide and variable region from SEQ ID NO: 1 were cloned into expression vector p2032. This vector contained a mouse immunoglobulin promoter, a human IgG1 CH1 constant region, the first cysteine in the a human IgG1 hinge sequence followed by PGK, and a GPT gene for selection of stable integration into the host cell genome. The completed CNTO95 heavy chain Fab expression plasmid, p2324, encoding SEQ ID NO: 3, was co-transfected with the CNTO95 light chain expression plasmid, p2330, into sp2/0 mouse myeloma cells. Cell clones with stable genomic integration of the plasmids were selected based on their resistance to mycophenolic acid in the presence of hypoxanthine. These clones were assayed for Fab expression by ELISA and western blot. The highest expressing clones were subjected to one round of subcloning, with the best subclone expressing 10 ug/ml. This clone, C1021A, was scaled up for further analysis.

The resulting Fab product was designated CNTO 119 and comprised SEQ ID NO: 3 and SEQ ID NO: 2). The C-terminus of the heavy chain bears a single cysteine which can be used effectively for conjugation reactions following mild reduction. The three C-terminal amino acids (PGK) are the same as the C-terminal residues of the full-length IgG1 heavy chain (including CNTO95 heavy chain).

Example 10

Preparation of Conjugated sFab-Targeted STEALTH Liposomes

A significant portion of the sFab starting material was in the oxidized disulfide form and was subjected to reduction using 10 mM DTE, 40° C., pH 6.0 for 60 minutes to form a free sulfhydryl for conjugation. Excess reductant was removed by passing the reduced sFab material over a desalting column using saline as the running buffer. The pH of the collected sFab fraction was adjusted to pH 6.0 and the protein concentration measured. Since the reduction process produces significant amounts of unwanted by-products (i.e., unassociated light and heavy chains), the sFab material was then subjected to oxidation by introduction of oxygen into the solution to reform the critical disulfide bond between the light and heavy chains that form sFab. Reformation of sFab was monitored by SEC-HPLC. After approximately 4.5 hours of the oxidation reaction, the sFab material was conjugated with MalPEG-DSPE (5:1 MalPEG-DSPE:sFab ratio) at room temperature for 1 hour. The solution was quenched for 10 minutes using 1 mM cysteine and run over a desalting column to remove unreacted cysteine. The resulting conjugated sFab material was loaded onto a SEC column (Sephacryl 300) to remove unconjugated protein with PBS as the running buffer. The resulting purity and yield of sFab-conjugate was 95% and 67%, respectively.

sFab-conjugate material was placed over a desalting column to exchange the external buffer to saline. Liposomes containing encapsulated doxorubicin, as described in Example 1 in saline, were inserted with sFab-conjugate at either 60° C. for 1 hour or 37° C. for 48 hour. The amount of sFab added to the liposomes was sufficient to achieve the desired ratio of 15 sFab ligands per liposome. After insertion, the sFab liposome solution was diluted to a final target concentration of 2 mg/mL with saline. The final formulations were in saline. sFab liposome samples were only tested on confocal microscopy to assay bioactivity.

Bioactivity results were negative for formulations inserted at 60° C. while marginal bioactivity of the formulations inserted at 37° C. was observed.

Example 11

Preparation of a Single Chain Anti-Alpha V Antibody 1. scFv Engineering

Single chain variable fragments (scFv) of antibodies are well-suited as targeting agents due to their small size and compatibility with the cysteine-based PEG coupling chemistry required to incorporate the targeting agent into the STEALTH® liposome. To this end, scFv derivatives of CNTO 95 were designed, engineered and expressed. Several variants were designed in order to overcome problems with expression. In one variant, the naturally occurring Arg-Arg amino acid pair, which frequently inhibits expression in *E. coli*, was mutated to Leu-Arg. The leucine substitution (R18L, an arg mutation to leu at the 18$^{th}$ amino acid of HC variable region) resulted in a substantial improvement of expression in *E. coli* cells using an arabinose inducible promoter (Xoma system, Xoma LLC, Berkeley, Calif.).

CNTO95 scFv variable heavy and light chain sequences were derived from CNTO95 Mab (U.S. Pat. No. 7,163,681). A flexible linker (Gly4Ser)$_3$ connects the variable regions to provide sufficient conformational flexibility for the pairing of the VH and VL domains of SEQ ID NO: 1 residues 1-119 and 2 residues 1-108, respectively. The construct was expressed transiently in HEK293 cells. The *E. coli* constructs were optimized for expression by engineering the codons that are considered rare in *E. coli* to more frequently used synonomous codons. All constructs contain a PelB signal sequence and a C-terminal 6×His tag followed by a Gly4Cys to allow purification and PEG conjugation to liposomes, respectively (SEQ ID NO: 5). The R18L derivative protein coding region was designed to be compatible with expression vectors established for other scFv such as the F5, directed against human ErbB2 selected from a scFv phage library (WO99/55367 and WO99/56129) and which all comprised the (G4S)3 linker. The resulting EcoRI and XhoI fragment was cloned into the pING3302 vector (Xoma), which vector has an arabinose inducible gene for expression and tetracycline resistant gene and is related to a previously described vector for Fab expression (Chowdhury, P. S., I. Pastan. 1999. Nat. Biotechnol. 17:568-572). Multiple variants of this construct series were generated to optimize the expression level of the scFv constructs, these included the construct without a His tag, or with a (G$_4$S)$_4$ linker, or with alternate heavy and light chain framework regions as shown in Table 11.

TABLE 11

Plasmid Expression Constructs

| | |
|---|---|
| 4016 | scFv CNTO 95 (EG0001). PelB-Vh-(G4S)x3-Vk-G4C, |
| 4017 | scFv CNTO 95 (EG0002). PelB-Vh-(G4S)x4-Vk-G4C |
| 4018 | scFv CNTO 95 (EG0003). PelB-Vh-(G4S)x3-Vk-His6tag-G4C |
| 4028 | scFv CNTO 95 (CNTBH117) PelB-Vh-(G4S)x3-Vk |
| 3202 | scFv F5 with histag (CNTOBH 120) in XOMA vector. |
| 3203 | scFv F5 with histag and Cys (CNTOBH 121) in XOMA vector.. |
| 3204 | scFv CNTO95 with (G4S)X3, histag and Cys (CNTOBH 122) in XOMA vector. |
| 4071 | scFv CNTO95 R18L (P3204). Change RR to LR on HC V-region |
| 4073 | scFv CNTO95 with (G4S)X4 linker but is otherwise identical to P3204 |
| 4072 | scFv CNTO95 R18L (P4073). Change RR to LR on HC V-region |
| 4225 | scFv CNTO95 R18L (P4071) without Cys |

2. ScFv CNTO95 Expression

For mammalian expression, HEK 293 cells were transiently transfected in serum-free media using the mammalian expression vector pCEP4 (Invitrogen), previously modified to contain the CMV-IE intron A. After 4 days, conditioned supernatant was tested for scFv protein expression by Western blot and ELISA. The plasmid comprising the CNTO95 scFv HCO R18L in pBeth vector was designated p4544.

For E. Coli, expression was performed using an arabinose inducible system obtained from Xoma, Inc. The DNA was transformed into E. coli E104 competent cells (competent cells were prepared by following a standard CaCl$_2$ solution method (T. Maniatis et al., 1982, *Molecular Cloning (A Laboratory Manual)*, Cold Spring Harbor Laboratory). A single colony was grown in 2 ml 2×YT medium with 25 ug/ml tetracycline at 37° C. overnight. The culture (diluted ⅕₀₀) was expanded in 250 ml 2×YT medium with 25 ug/ml tetracycline. After the culture reached OD600 at 0.6, it was induced with 0.1% of L-arabinose at 25° C. overnight and harvested by centrifugation at 10K for 15 min. The supernatant was used to detect the expression of the expected protein by Western blotting. The pellet was lysed with 20 ml B-PERII bacterial protein extraction buffer (Pierce), followed by centrifugation, and the resulting supernatant was processed to purify the induced protein using Talon resin (BD Biosciences), according the manufacturer's instruction.

Initial expression in the Xoma system produced very low levels of scFv protein. Tandem arginine residues were identified in the FR1 region of the heavy chain at positions 18 and 19. Since double arginine amino acid residues have been shown to be potentially detrimental for protein expression, arginine 18, the first arginine in the doublet, was reverted to leucine, LR, which corresponds to the human VH germline sequence having the closest homology and derived from Ig H-chain V-region (DP-46) (Referenced as NCBI Accesion No. CAA78216) and as shown below. The 28 kD scFv protein was only detected in E. coli supernatant fractions when variants with the R18L mutation were expressed.

3. ScFv CNTO95 Detection

Supernatant, cell lysate and purified protein were separated by electrophoresis on 4-12 SDS-polyacrylamide gels and transferred to PVDF membranes. The membranes were blocked with 5% nonfat dry milk in TBS containing 0.05% TWEEN 20® (wash buffer) at room temperature for 1 hr.

To detect scFv protein, two distinct antibodies were used for Western blotting. The first one was anti-his antibody, while the second one was anti-CNTO95 idiotypic antibody (C508, murine anti-CNTO95), which has binding affinity to CNTO95 variable domains. For anti-his Western blot, the membrane was incubated with peroxidase-conjugated anti-His antibody (1:5000 dilution), and the his-tag protein was detected using ECL Western Blotting Analysis System (Amersham Biosciences). For the anti CNTO95 id Western blot, the capture antibody was C508 antibody (1:1000 dilution). Peroxidase-conjugated anti-mouse antibody (1:5000 dilution) was used as the secondary antibody, followed by detection of bound protein using the ECL Western Blotting Analysis System Amersham Biosciences). Using the anti-his antibody as a probe, the Western Blot showed that the 28 kD scFv protein was only detected in variants with the R18L mutation.

4. scFv Binding Affinity:

The binding affinity of scFv CNTO95 was measured using a validated sandwich enzyme-linked immunoassay. The 96-well plates (Coasta, high binding plate) were coated with 100 ul of integrin αvβ3 or αvβ5 (Chemicon International Inc.) at 1 ug/ml in coating buffer (0.75 g Na$_2$CO$_3$ and 1.45 g NaHCO$_3$ in 500 ml H$_2$O) and incubated overnight at 4° C. The plates were blocked with Superblock blocking buffer in PBS (Pierce) at room temperature for 1 hr. Wells were washed with PBS+0.05% TWEEN 20® between each step. Controls and scFv purified protein were diluted serially at 3-fold with TBST, and added to the coated wells in duplicate, and incubated at 37° C. for 2 hrs. Two methods were used to detect the binding. For anti-his ELISA 1:1000 diluted HRP mouse anti-his antibody were added to each well and incubated for 1 hr. For the anti-CNTO95 anti-idiotype ELISA, an aliquot of 1:1000 diluted 1 mg/ml C508 antibody was added to each well and incubated for 1 hr. Peroxidase-conjugated anti-mouse antibody (1:5000 dilution) was used as the secondary antibody, followed by incubation at the plate for 1 hr at 37° C.

The ELISA was developed using OPD tablet (Sigma) in development buffer for 15 min at room temperature. The colorimetric detection was stopped with 1N H$_2$SO$_4$. The binding affinity was measured in a plate reader at 490 nm. In the assay, purified CNTO95 scFv protein from E. coli bound both αvβ3 and αvβ5 integrin proteins (FIG. 14) as shown for integrin-coated ELISA plates and was detected by HRP anti-His Ab as well as the anti-CNTO95 Ab (c508).

ScFv vs Mab Binding Affinity to Integrin Competition Assay:

To compare the binding affinity of scFv CNTO95 and CNTO 95 mAb, the 96-well plates were coated with 100 ul of integrin αvβ3 or αvβ5 as described above. CNTO95 mAb was added to each well at 0.8 nM for αvβ3 coated plate or 0.2 nM for αvβ5 coated plate. Controls and scFv purified protein

```
(1)                CNTO95 V-region                    (50)
   QVQLVESGGGVVQPGRSRRLSCAASGFTFSRYTMHWVRQAPGKGLEWVAV    SEQ ID NO: 10
   QVQLVESGGGVVQPGRSLRLSCAASGFTFSSYAMHWVRQAPGKGLEWVAV    SEQ ID NO: 11
              Ig H-chain V-region (DP-46)

Figure 15A:
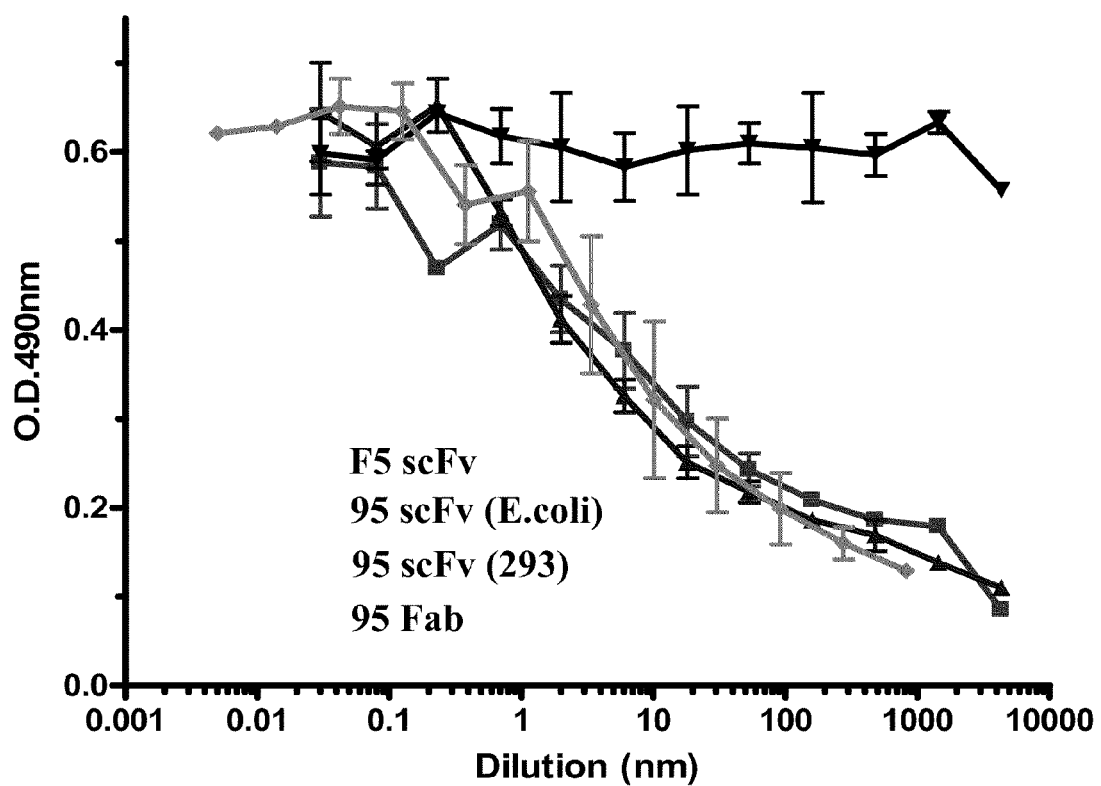
FIG. 15A-15B are graphs showing a competitive binding of assay between CNTO95 derived scFV and the native CNTO95 to alphaVbeta3 (A) or alphaVbeta5 (B) coated plates with CNTO95 Fab a positive and anti-her2 scFv (F5) a negative control. The detection antibody was HRP anti-human Fc.
Figure 15B:
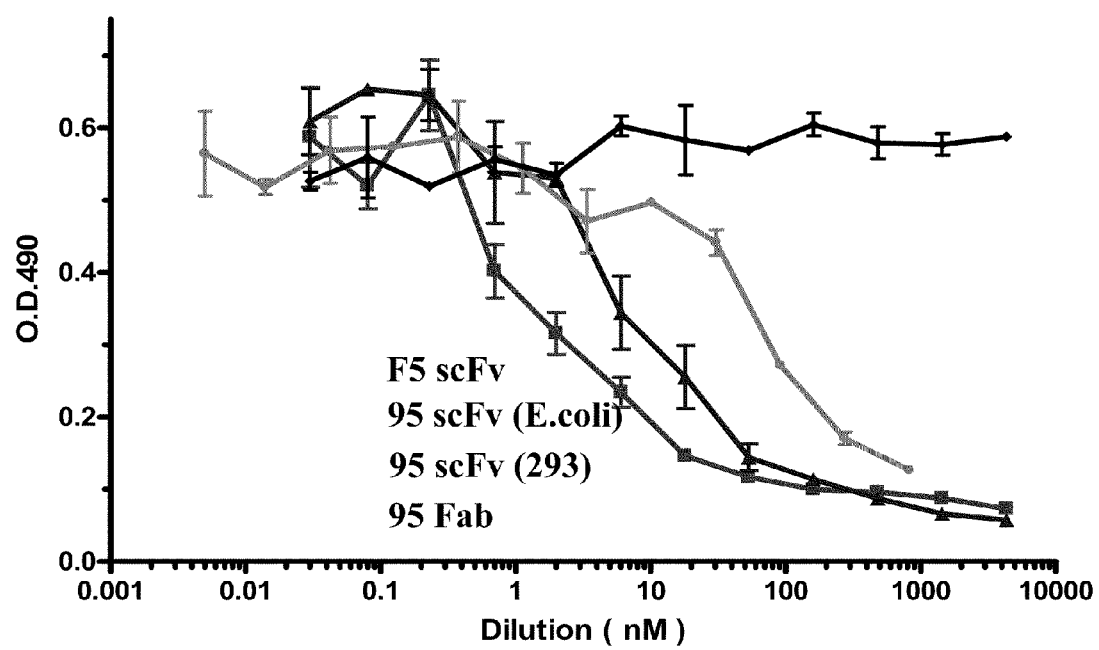

(51)               CNTO95 V-region                    (98)
   ISFDGSNKYYVDSVKGRFTISRDNSENTLYLQVNILRAEDTAVYYCAR      SEQ ID NO: 10
   ISYDGSNKYYADSVKGRFTISRDNSKNTLYLQMNSLRAEDTAVYYCAR      SEQ ID NO: 11
              Ig H-chain V-region (DP-46)
``` diluted serially at 3-fold with TBST were added to the coated wells in duplicate. The mix of CNTO95mAb and sFv were incubated at 37° C. for 2 hrs. The detection antibody was 1:10K dilution of peroxidase conjugated affinipure F(ab')$_2$ fragment Goat anti-human IgG, Fc fragment specific (minimal cross reaction to Bovine, Horse and mouse serum protein) (Jackson Immunoresearch). The antibody was incubated on the plate 1 hr at 37° C. and the color was developed and read as above. CNTO95 mAb binding to both alphaV-integrins was competed with the CNTO 99 scFv (FIGS. 15A and B). The assay indicates CNTO95 scFv effectively competes with the Mab for integrins binding in a manner comparable to the F(ab)'2 protein.

Summary

The optimized CNTO95 scFv is composed of an immunoglobulin heavy-chain leader sequence and heavy and light chain variable regions that are joined by an inter-chain (Gly$_4$Ser)$_3$ linker which allows conformational flexibility. A Pel B signal sequence was placed upstream of the antibody coding sequence with in the vector to facilitate secretion of the antibody. The *E. coli* constructs were further optimized for expression by engineering the codons that are considered rare in *E. coli* to more frequently used synonymous codons. All constructs contain a C-terminal 6×His tag, to facilitate purification, followed by a Gly$_4$Cys to allow chemical conjugation via the free sulhydryl to, e.g. a thiol-reactive derivatized PEG, for insertion into liposomes. The disruption of an arginine doublet in the heavy chain sequence (18-19) by the R18L mutation proved essential for secretion and recover of the 28 kD scFv protein. Variants with different linker lengths did not alter expression levels.

Example 12

Preparation of Conjugated scFv-Targeted STEALTH® Liposomes

As a significant portion of the scFv starting material was oxidized and in the dimeric (disulfide form) the scFv was subjected to reduction using 10 mM DTE, 30° C., pH 7.0 for 60 minutes to form a free sulfhydryl for conjugation. Excess reductant was removed by passing the scFv over a desalting column using saline as the running buffer. The pH of the collected scFv fraction was adjusted to pH 6.0 and the protein concentration measured.

Liposomes containing encapsulated doxorubicin, as described in Example 1, were inserted with maleimide-PEG-lipid (MalPEG-DSPE) at approximately 800 MalPeg-DSPE per liposome at 60° C. for 1 Hr. The appropriate amount of scFv was added to the MalPEG-DSPE inserted liposomes to achieve the desired ratio (15, 40 or 90 to 1). It was assumed that 50% of the scFv would conjugate to the liposomes based on previous work. The conjugation proceeded at room temperature for 2 hours followed by overnight refrigeration. Each formulation was quenched by adding 1 mM Cysteine for 10 min and passed over a size-exclusion column to remove non-conjugated scFv (monomer and dimer) and free cysteine. The final formulations were in saline, 10 mM histidine at pH 6.5.

Example 13

Cytotoxicity Assays Using scFv-Targeted STEALTH® Liposomes

Human melanoma cells (A375.S2, ATCC CRL 1872), passage 3 to 9, were incubated in EMEM (Eagle's Minimum Essential Medium, ATCC Cat No. 30-2003) containing 10% FCS (ATCC Cat No. 30-2021). On the day of the assay, cells were scraped from the surface of the culture flask and pipetted up and down using serum containing media to make single cell suspension. The cells were rejuvenated by suspending them in complete medium at 37° C. for 1 hour with mild shaking. Thereafter, the cells were pelleted and resuspended in serum-free medium at 200K in 1 ml in a 5 ml polypropylene round-bottom tube (BD Falcon).

Freshly prepare anti-alphaV scFv (CNTO99) targeted DOXIL® liposomes prepared with varying ratios of antibody to liposome: 15:1, 40:1, 90:1 were diluted by serial 5-fold dilutions (1.6, 8, 40 and 200 ug/ml of DOXIL as doxorubicin with a prewarmed (37° C.) solution of 10% sucrose+ions (1 mM CaCl2, 1 mM MgCl2, 10 uM MnCl2), pH 5.7. Untargeted DOXIL® and doxorubicin (DXR) was prepared similarly. Untreated group: A375.S2 cell only be incubated with diluting solution, 10% sucrose+ions pH 5.7, at 37° C.

To the respective labeled tubes containing the cell suspensions, was added 0.1 ml of scFv-targeted DOXIL®, DOXIL®, or DXR treatment solution. The tubes were shaken to mix and incubated at 37° C. for 10 min, with mild agitation (140 rpm on an orbital shaker). Treatments were stopped by adding 1.0 ml of 37° C. cell culture medium without FBS, vortexing briefly, and pelleting the cells at room temperature. The supernatant was discarded and cells resuspended in 1 ml of 37° C. cell culture medium without FBS. Washing was repeated twice and the cells finally resuspended in 2.0 mL of cell culture medium with FBS (37° C.). The cells were then counted and seeded at 2,000 cells/200 µl into each well of the 96 well plate. The plates were incubated at 37° C. for 3 days and 6 days at which time the cell number was quantitated using a CellTiter 96®AQueous One Solution (Promega) according to the manufacturers instructions using a Spectra Max 250, Molecular Devices spectrometer set at 490 nm.

Figure 16:
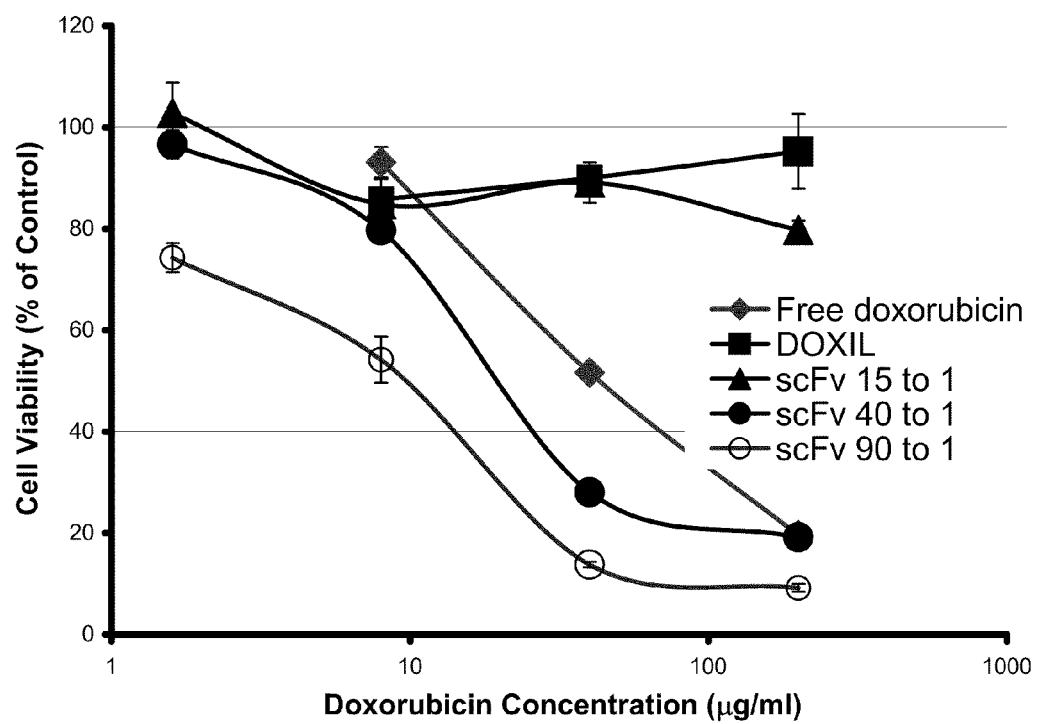
FIG. 16 shows a graph of the relationship between cell viability and treatment with various concentration of doxorubicin in different compositions: free doxorubicin, as liposomal doxorubicin (DOXIL®), or targeted liposomal doxorubicin using scFV on the surface of the liposome at a ratio of targeting ligand: liposome of 15:1, 40:1, and 90:1.

The results shown in FIG. 16 indicate that liposomes with greater than 15 scFv as targeting ligand on the surface are more effective in killing tumor cells (or preventing tumor cell growth) than untarget liposomes or free doxorubicin.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. An antibody derived targeting-ligand capable of monovalent binding and having specificity for alpha V integrin comprising:
   (a) a first polypeptide domain comprising the light chain variable region comprising residues 1-108 of SEQ ID NO: 2;
   (b) a second polypeptide domain comprising the heavy chain variable region comprising residues 1-119 of SEQ ID NO: 1, wherein the heavy chain variable region has a leucine substitution at the 18$^{th}$ amino acid;
   (c) further comprising at least one peptide linker linking said first and second polypeptide domains into a single chain Fv polypeptide wherein the linker has an amino acid sequence of the formula (Gly$_4$Ser)$_n$ of SEQ ID NOS: 6-9 where n is an integer of 1-4: and wherein the targeting ligand retains specificity for at least one alpha V integrin.

2. The antibody derived targeting-ligand of claim 1 where n is 3.

3. A pharmaceutical composition comprising the antibody derived targeting-ligand of claim 1 and a pharmaceutically acceptable carrier.

4. A pharmaceutical composition comprising the antibody derived targeting-ligand of claim 1 covalently linked to, or conjugated to a hydrophilic polymer, wherein the hydrophilic polymer is further covalently linked to a lipid, an active molecule, or a reporter molecule.

5. A pharmaceutical composition comprising the antibody derived targeting-ligand of claim 4, in which the hydrophilic polymer is inserted into the surface of a liposome.

6. The composition according to claim 5, wherein the liposome has an anti-neoplastic agent encapsulated within.

7. A composition according to claim 6, wherein the anti-neoplastic agent is selected from a radiopharmaceutical, an estrogen receptor modulator, a retinoid, a topoisomererase inhibitor, a cytotoxin, an alkylating agent, a nitrogen mustard, a nitrosourea, an anti metabolite, a mitotic inhibitor, and a radiosensitizer.

8. A composition according to claim 7, wherein the anti-neoplastic agent is doxorubicin.

* * * * *